US009322823B2

United States Patent
Denomme et al.

(10) Patent No.: US 9,322,823 B2
(45) Date of Patent: Apr. 26, 2016

(54) METHOD AND APPARATUS FOR CHEMICAL DETECTION

(71) Applicant: Nicoya Lifesciences Inc., Waterloo (CA)

(72) Inventors: Ryan Cameron Denomme, Kitchener (CA); John Alexander Gordon Dick, Mississauga (CA)

(73) Assignee: Nicoya Lifesciences Inc., Waterloo (CA)

( * ) Notice: Subject to any disclaimer, the term of this patent is extended or adjusted under 35 U.S.C. 154(b) by 0 days.

(21) Appl. No.: 14/216,042

(22) Filed: Mar. 17, 2014

(65) Prior Publication Data

US 2014/0271366 A1    Sep. 18, 2014

Related U.S. Application Data

(60) Provisional application No. 61/798,450, filed on Mar. 15, 2013.

(51) Int. Cl.
*G01N 15/06* (2006.01)
*G01N 33/00* (2006.01)
*G01N 33/48* (2006.01)
*G01N 33/543* (2006.01)
*G01N 21/552* (2014.01)

(52) U.S. Cl.
CPC ........ *G01N 33/54373* (2013.01); *G01N 21/554* (2013.01)

(58) Field of Classification Search
CPC ........ G01N 15/06; G01N 33/00; G01N 33/48
USPC ............................. 422/50, 82.05, 68.1; 436/43
See application file for complete search history.

(56) References Cited

U.S. PATENT DOCUMENTS

| | | | |
|---|---|---|---|
| 8,085,405 B2 * | 12/2011 | Ogawa | 356/445 |
| 2002/0142480 A1 | 10/2002 | Natan | |
| 2008/0117423 A1 * | 5/2008 | Ogawa et al. | 356/445 |
| 2008/0213814 A1 * | 9/2008 | Gerion et al. | 435/21 |
| 2009/0009756 A1 | 1/2009 | Yamamichi et al. | |
| 2009/0041404 A1 * | 2/2009 | Stoddart | 385/12 |
| 2012/0208174 A1 * | 8/2012 | Galush et al. | 435/5 |
| 2013/0135617 A1 | 5/2013 | Pris et al. | |

OTHER PUBLICATIONS

Dotzauer et al., "Catalytic Membranes Prepared Using Layer-by-Layer Adsorption of Polyelectrolyte/Metal Nanoparticle Films in Porous Supports", Nano Letters, vol. 6, No. 10, 2006. pp. 2268-2272.
Eftekhan et al., "Nanoholes as Nanochannels: Flow-through Plasmonic Sensing", Analytical Chemistry, vol. 81, No. 11, Jun. 1, 2009, pp. 4308-4311.
Govyadinov et al., "Anodic Aluminum Oxide Microchannel Plates", Nuclear Instruments and Methods in Physics Research, vol. 419, 1996, pp. 667-675.
Shao et al., "Optical Fiber LSPR Biosensor Prepared by Gold Nanoparticle Assembly on Polyelectrolyte Multilayer". Sensors, vol. 10, 2010, pp. 3585-3596.

* cited by examiner

*Primary Examiner* — Brian J Sines
(74) *Attorney, Agent, or Firm* — Blake, Cassels & Graydon LLP; Leah Rodin

(57) ABSTRACT

Provided herein is a sensing apparatus comprising, at least one LSPR light source, at least one detector, and at least one sensor for LSPR detection of a target chemical. The sensor comprises a substantially transparent, porous membrane having nanoparticles immobilized on the surface of its pores, the nanoparticles being functionalized with one or more capture molecules.

14 Claims, 24 Drawing Sheets

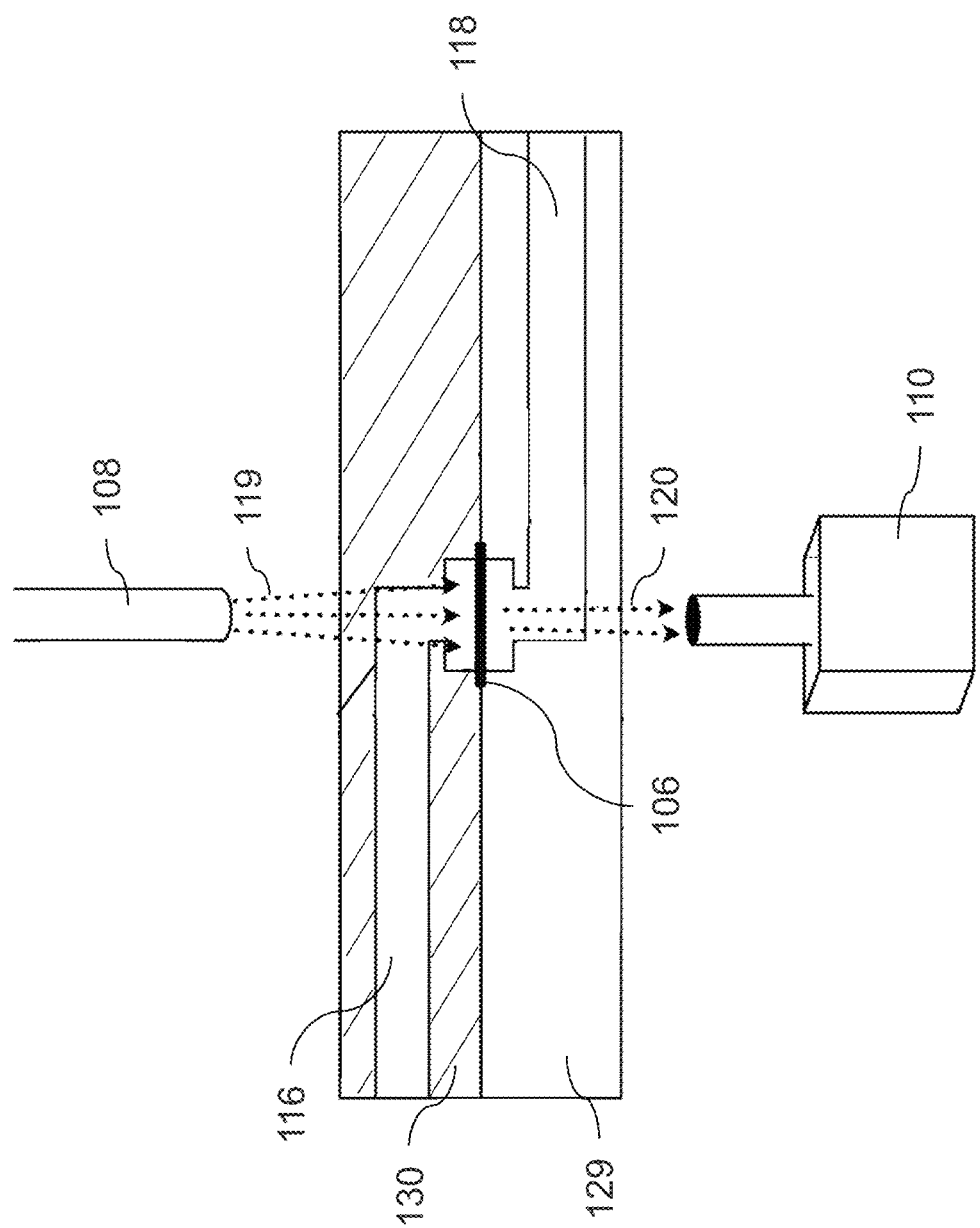

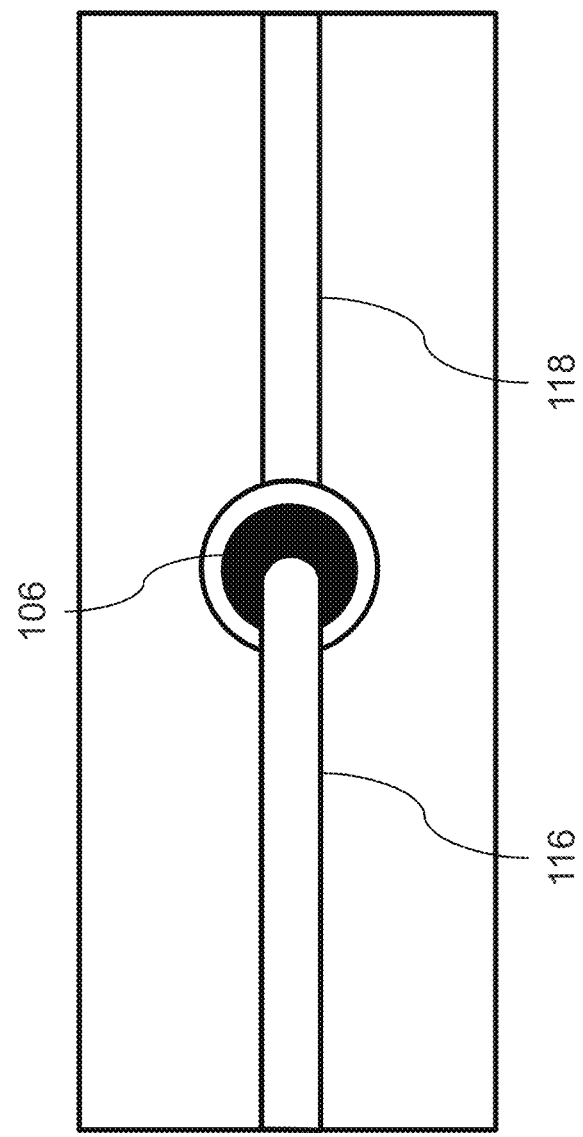

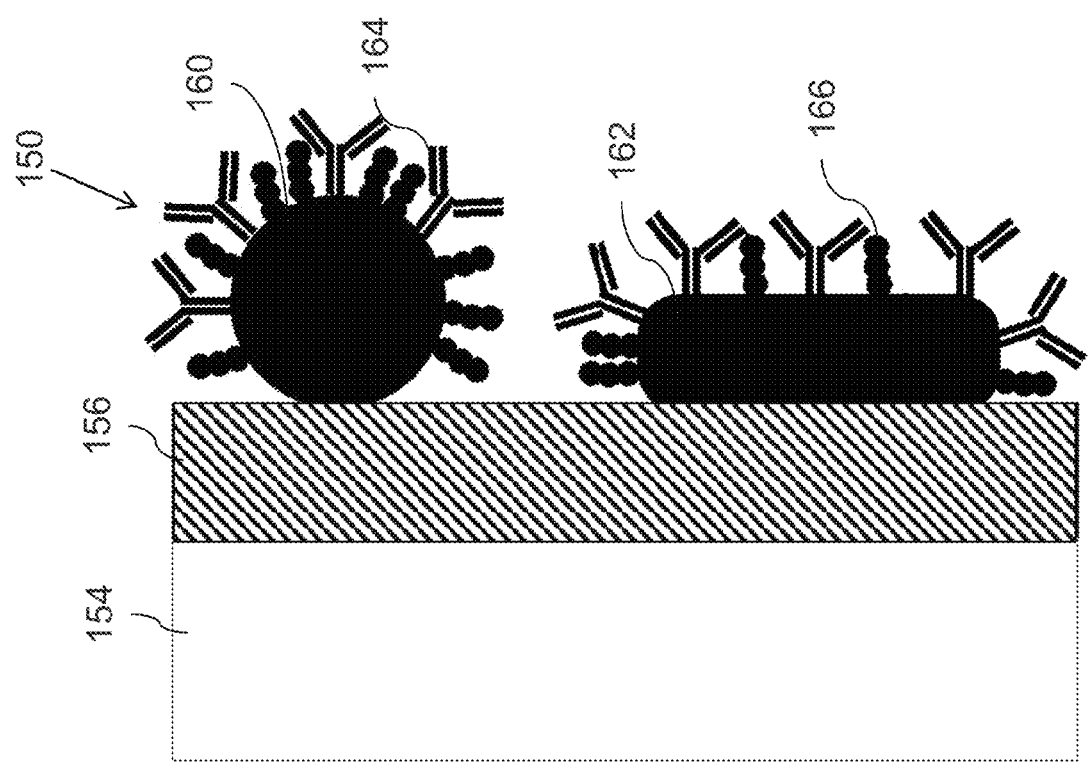

METHOD AND APPARATUS FOR CHEMICAL DETECTION

CROSS REFERENCE TO PRIOR APPLICATIONS

The present application claims priority under Paris Convention to U.S. Application No. 61/798,450, filed Mar. 15, 2013, the entire contents of which are incorporated herein by reference.

TECHNICAL FIELD

The following relates generally to a method and apparatus for chemical detection.

BACKGROUND

Determining the presence and concentration of bio-molecules and other chemicals in a fluid is important in many applications. For example, an instrument that can determine the concentration of one or more specific chemical targets in a gas or liquid containing various chemicals may have applications in medical diagnostics, high throughput drug development, environmental testing, defense and laboratory-based research. Such techniques are also important for biomolecular interaction analysis in which reaction kinetics (on and off rates), affinity, and specificity are determined, along with other important parameters.

A common strategy to detect a chemical target is to use an instrument with a capture molecule which binds to the target chemical of interest and a transducer that allows the user to observe the binding event. Preferably, the capture molecule preferentially or exclusively binds to the chemical target. In the case of bio-molecular targets, antibodies, aptamers and polymers are used as capture molecules.

Optical transduction of binding events is a common detection method. To optically observe a binding event between a capture molecule and a target, various spectrometric techniques can be employed. These techniques may require that capture molecules be labeled with a transducer or tag, such as a fluorescent molecule for fluorescence spectroscopy or a Raman tag for Raman spectroscopy. A technique used for medical diagnostics is enzyme linked immunosorbant assay (ELISA) that utilizes fluorescently-labeled antibodies to detect various target chemicals, including bio-molecules, in human biological fluids to detect disease.

Labeled assays may be disadvantageous because labeled capture molecules may have adverse effects on assay results due to steric hindrances. Assays comprising labeled capture molecules are also not compatible with real-time testing. Labeling capture molecules also increases device complexity and cost.

Label-free assays, which do not require the addition of a labeled capture molecule, are advantageous because the target chemical is not sterically hindered from binding to the capture molecule by a label. Label-free assays may also measure binding events in real time, which improves the performance and sensitivity of the assay. Label-free assays can also be used for biomolecular interaction analysis as they provide real time data.

Metal nanoparticles, between 1 nm and 1000 nm in various dimensions, may be used as transducers in diagnostic assays. Some nanoparticle based diagnostic assays are 'label-free'. Metal nanoparticle transducers can be used to monitor binding events in real time without additional labels through a phenomenon known as localized surface plasmon resonance (LSPR).

LSPR is a phenomenon associated with noble metal nanoparticles that creates sharp spectral absorbance and scattering peaks and produces strong electromagnetic near-field enhancements. These spectral peaks can be monitored using absorbance spectroscopy. The spectral peak changes with refractive index changes in the immediate vicinity of the nanoparticle surface. When chemical targets are bound near the surface of a metal nanoparticle, a shift in the spectral peak occurs due to changes in the local refractive index. This can be used to determine the concentration of a specific target in a complex medium.

LSPR sensors operate through the immobilization of metal nanoparticles onto a flat surface. The nanoparticles are functionalized with specific capture molecules, which may be an antibody. The sample fluid of interest is flowed over the top of the metal nanoparticles, the target chemicals of interest bind to their respective capture molecules, and the overall spectral peak of the sensor shifts according to the concentration of the chemical target on the capture molecules. In order to measure this shift, reflectance absorbance spectroscopy may be employed. Quantification is possible through comparing results to a previously-developed standard curve.

However, LSPR sensors suffer from low sensitivity and inadequate detection limits for a number of reasons.

LSPR sensors with nanoparticles on planar surfaces operate by flowing the sample longitudinally over the surface. In order for the sensor to determine the target concentration with the highest sensitivity and accuracy, the sensor must reach chemical equilibrium. Equilibrium occurs when the maximum fraction of capture molecule binding sites are occupied by chemical targets on the sensor surface, resulting in the largest sensor response in a reaction-limited assay. Lengthy incubation times are required to reach equilibrium.

Long incubation times are not suitable for many applications including point-of-care diagnostics. Long incubation times may be problematic for types of planar sensors other than LSPR sensors.

Reflectance LSPR signals from nanoparticles on a planar surface are also weak, leading to poor signal to noise ratios and poor detection limits. This may be addressed by using nanostructured surfaces to increase the surface area and nanoparticle density, resulting in a larger LSPR signal. However, this has the negative effect of increasing the time it takes to reach equilibrium and obtain the highest fraction of surface coverage since the number of surface sites is greatly increased. Essentially this improves signal to noise ratio but worsens the time to reach equilibrium, and overall does not greatly improve sensor performance. Moreover, these techniques rely on reflection measurement systems because the materials used are opaque at LSPR wavelengths and will not allow for transmission measurements.

SUMMARY

In one aspect, there is provided a sensor for LSPR detection of a target chemical. The sensor comprises a substantially transparent, porous membrane having nanoparticles such as metal nanoparticles immobilized on the surface of its pores, the nanoparticles being functionalized with one or more capture molecules.

In a further aspect there is provided an sensing apparatus comprising at least one LSPR light source; at least one detector and at least one sensor for LSPR detection of a target chemical located between the detector and the light source, the sensor comprising a substantially transparent, porous membrane, the membrane comprising nanoparticles immobilized on the surface of its pores, the nanoparticles being functionalized with one or more capture molecules.

BRIEF DESCRIPTION OF THE DRAWINGS

Embodiments will now be described by way of example only with reference to the appended drawings wherein:

FIG. 2 is a side view of the fluidic cartridge of FIG. 1;

FIG. 3 is a top view of a fluidic cartridge of the chemical sensor of FIG. 1;

FIG. 4C is an enlarged side view of a pore of FIG. 4A depicting functionalized metal nanoparticles;

DETAILED DESCRIPTION

It has now been realized that the long incubation times associated with existing LSPR sensors are due, at least in part, to the diffusion time required for target chemicals in a fluid to reach capture molecules on the sensor. One method to reduce the diffusion time of the chemicals in the fluid is to reduce the diffusion length. It has been realized that the diffusion length may be reduced by flowing a higher proportion of the sample a closer distance to the capture molecules. Specifically, it has been found that the diffusion time may be reduced by flowing a sample fluid through a relatively narrow-size pore having capture molecules immobilized on its surface. This causes the mean distance between target chemicals and capture molecules in a set volume of sample fluid to be reduced with respect to flowing the same volume of sample fluid over a planar surface comprising capture molecules.

Figure 1:
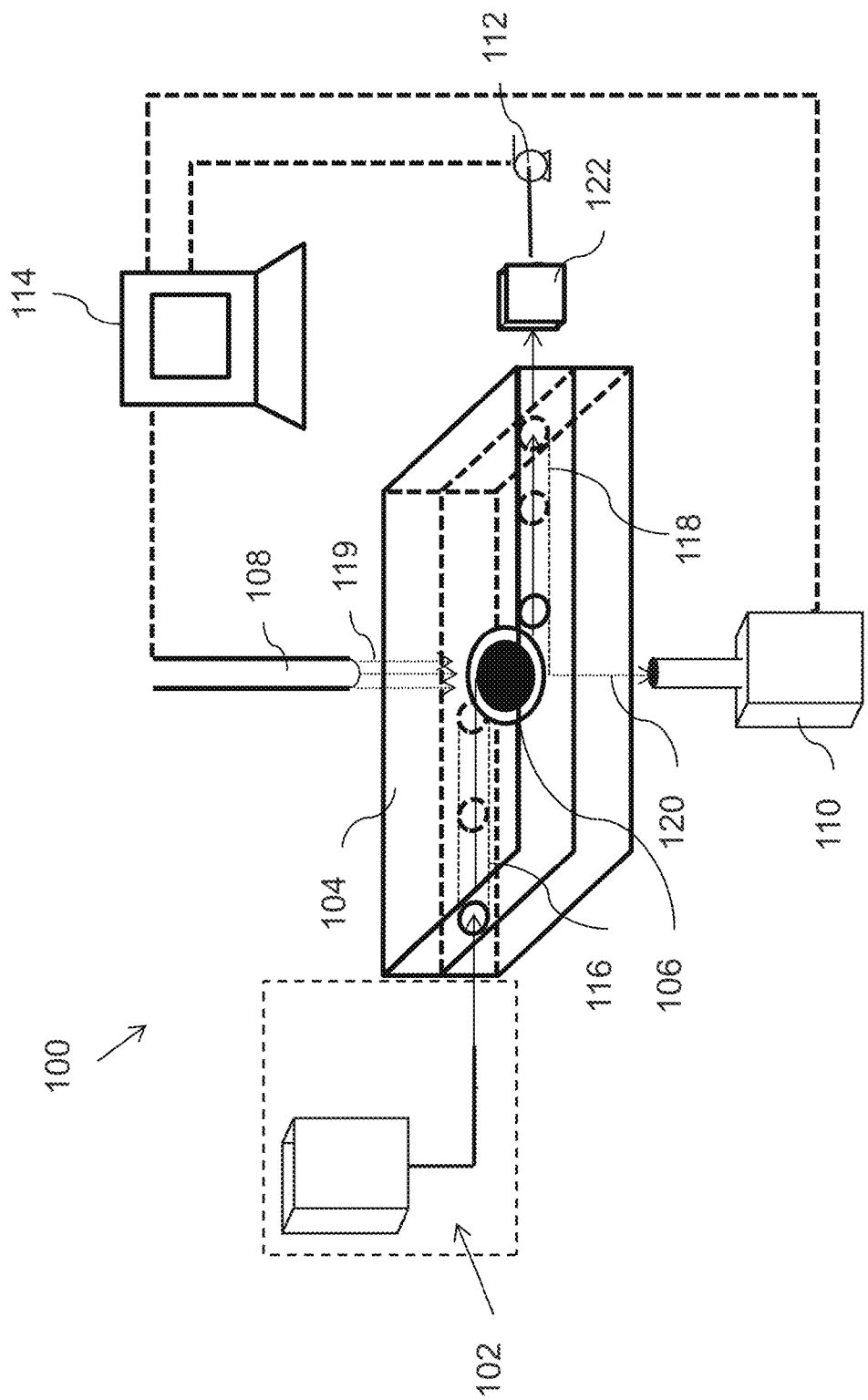
FIG. 1 is a diagram of a transmission-based three-dimensional chemical sensing system.

Referring now to FIG. 1, an example three-dimensional chemical sensing system 100 is provided. The chemical sensing system 100 comprises a fluidic cartridge 104, an inlet port 102, a signal processor 114, a light source 108 for LSPR measurement, and a detector 110. The chemical sensing system 100 may further comprise an outlet reservoir 122 and a fluid driving element such as a pump 112 or pressure source (not shown).

The pump 112, the light source 108, and the detector 110, may be electrically powered, for example, by a battery, a power outlet, or a combination of both. The chemical sensing system 100 may be located within a housing (not shown), for example, a portable housing such as a hand-held housing.

Inlet port 102, which is in communication with a fluid inlet 116, is operable to receive a fluid sample, for example from a syringe, and feed the fluid sample to the fluid inlet 116. The inlet port 102 may further comprise, or be linked to, a filter or mixing element to filter, pre-treat or mix a sample fluid.

The inlet port 102 may vary in form depending on the type of fluid sample that is being tested. For example, in the case of a blood sample for biological diagnostics, a sterile needle in a lancing device may be employed to obtain the sample similar to a glucose monitor. It will be appreciated that the inlet port 102 may comprise various other forms including Luer taper fittings, press fittings, or an open reservoir. It will be appreciated that the inlet port 102 may be built into the fluidic cartridge 104.

Referring now to FIGS. 2 and 3, the fluidic cartridge 104 comprises a fluid inlet 116, a sensor 106, and a fluid outlet 118. The fluid inlet 116 is fluidically connected to the sensor 106 and thereby, operable to deliver fluid to the sensor 106 to cause one or more target chemicals in the sample fluid to bind to capture molecules in the sensor 106, as is further described herein. It will be appreciated that the same sample may be transported to two or more sensors, for example, in a multiplexed design as demonstrated below with reference to FIG. 7.

The fluidic cartridge 104 may be disposable or designed for repeated use. The fluidic cartridge is composed of a material that is substantially optically transparent in the LSPR wavelengths being used. For example, polydimethylsiloxane (PDMS), is optically transparent over many LSPR wavelengths. In the example of FIG. 3, the sensor 106 is sandwiched between two layers of PDMS. Other transparent materials could be used to form the fluidic cartridge including, glass, poly(methyl methacrylate) (PMMA), cyclic-olefin polymer, or another material through which micro-channels may be formed to produce the fluid inlet 116 and the fluid outlet 118.

The fluid outlet 118 is also fluidically connected to the sensor 106 to receive fluid from the sensor 106 and allow fluid to egress from the sensor 106. Optionally, the fluid outlet 118 may deliver, to the outlet reservoir 122, fluid that has passed through the sensor 106. Alternatively, the fluidic cartridge 104 may retain the sample.

Although the fluid inlet 116 and fluid outlet 118 are shown in the simplest form in FIG. 3, the fluid inlet 116 and fluid outlet 118 may take different routes through the fluidic cartridge depending on specific requirements such as flow rate and sample volume or the need for mixing and pre-treatment steps. The dimensions and path of the fluid inlet 116 and fluid outlet 118 may be chosen depending on the desired fluid speed and mixing properties.

A pump 112, or other fluid driving element, may optionally drive the fluid from the inlet fluid channel 116, through the sensor 106 and out of the fluidic cartridge through the fluid outlet 118. For example, the fluid driving element may also comprise a pressure source or a vacuum source at the outlet port 118. The pump 112 can be controlled by the signal processor 114 or other controller. The direction of fluid flow can be rapidly and automatically switched via software control to move the sample back and forth transversely through a membrane in the sensor 106, allowing for prolonged interaction times with a small sample volume, thereby potentially increasing the performance of the sensor 106.

Alternatively, the fluid may be driven through the sensor 106 using, for example, electro-osmotic pumps, gravity, wicking of a membrane, or be driven by a syringe or other fluid source at the inlet port 102.

The signal processor 114 comprises, or is linked to, a memory, a processor, and a user interface which may include a display and an input device such as a touch screen or keyboard and mouse. The signal processor 114 may be linked to another input device, for example, a barcode scanner, an RFID scanner, or an NFC reader to identify a fluidic cartridge comprising an identifier, for example, a barcode, RFID tag, or NFC chip. It will be appreciated that other identification methods may be used including, for example, image analysis or a simple identification code which may be entered by the user. The identifier may comprise, or be linked to fluidic cartridge information such as relevant standard curves, the type of sensor being used, manufacturing date, etc.

The signal processor 114 may, in various examples, comprise a computer such as a laptop computer, desktop computer, microcomputer, cloud-based processor, or a mobile device. The memory of the signal processor 114 may contain fitting algorithms and standard curves. The signal processor 114 may be linked to one or more of the pump 112, light source 108, or detector 110 via a wired connection, for example a local area network or USB connection. Alternatively, or in addition, signal processor 114 may be linked to one or more of the pump 112, light source 108, or detector 110 via a wireless connection such as Bluetooth, Wi-Fi, or cellular connection. In some embodiments, the signal processor 114 may be located remotely from the fluidic cartridge 104.

The signal processor 114 may control the light source 108 to emit light into the sensor 106. An example light source 108 comprises a white light emitting diode (LED) and is coupled to a detector 110 comprising a UV-visible spectrometer. White light sources other than LEDs such as halogen bulbs and others such as red, green, and blue LEDs separate or combined together, may also be used. A light source for the visible range (400-800 nm) could be a white light source such as a halogen bulb or an LED, a combination of colored LED light sources such as red, blue, and green, a single colored LED light source, or a laser at a specific wavelength. For operation below the visible range (100-400 nm) of the spectrum, an ultraviolet (UV) light source such as a UV LED could be used. For operation above the visible range (800-2500 nm) an infrared (IR) source such as an IR LED could be used.

The detector 110 may comprise a charge coupled device, a photodetector, a spectrometer, a photodiode array, or a combination thereof, to obtain LSPR light intensity readings. The detector 110 may comprise a spectrometer or photodetector designed for parts of the electromagnetic spectrum outside the visible range, including the ultraviolet (UV) range, the near infrared (NIR), or IR range. The detector 110 may comprise a combination of two types of detectors, for example, a photodetector and a spectrometer. The detector 110 is selected in combination with an appropriate light source 108.

The light emitted by the light source 108 is transmitted though the fluidic cartridge 104 and sensor 106 and is received, at least in part, by a detector 110. As mentioned above, the fluidic cartridge 104 and sensor 106 must be at least partially transparent to the LSPR wavelengths emitted by the light source 108. The detector 110 generates a transmission signal, for example a digital transmission signal, based on the light transmitted through the sensor 106 and provides the signal to the signal processor 114. The signal processor 114 is operable to produce a spectrograph based on the transmission signal. The signal processor 114 may also be operable to select an output based on a predetermined transmission signal or a comparison between the transmission signal and one or more reference signals or thresholds. For example, the signal processor 114 may output the concentration of a target chemical based on a transmission signal that is consistent with one or more reference signals, or exceeds a threshold of an established reference signal. The signal processor may also be used to determine biointeraction analysis parameters between the target and capture molecule, which may include reaction kinetic information (on and off rates), affinity, and specificity. A simple photodetector may be used to measure intensity changes due to the spectra shifts.

In the example of FIG. 1, the sensor 106 is substantially planar and is located laterally between the path of the light source 108 and the detector 110. As a sample fluid flows through the sensor, the light source 108 emits light and the spectrometer 110 receives light continuously, or at predetermined intervals, to monitor changes in the resonance peak of the detected light. The light source 108 and detector 110 may be arranged for maximal illumination of the sensor and maximal capture of the light transmitted through the membrane, respectively. FIG. 1 shows a transmission based LSPR arrangement, wherein the light source 108 shines through the membrane and to the detector 110.

It has been found that to address, at least in part, the sensitivity of LSPR-based chemical detection, a three-dimensional porous membrane is used as a substrate for sensor 106. Functionalized metal nanoparticles are immobilized within the pores of the membrane and a sample is flowed through the pores. Such a sensor design may be referred to herein as a transmission-based three-dimensional sensor (T3D). The three-dimensional porous membrane is substantially transparent for the wavelengths of incident light that are used to obtain a signal.

Figure 4B:
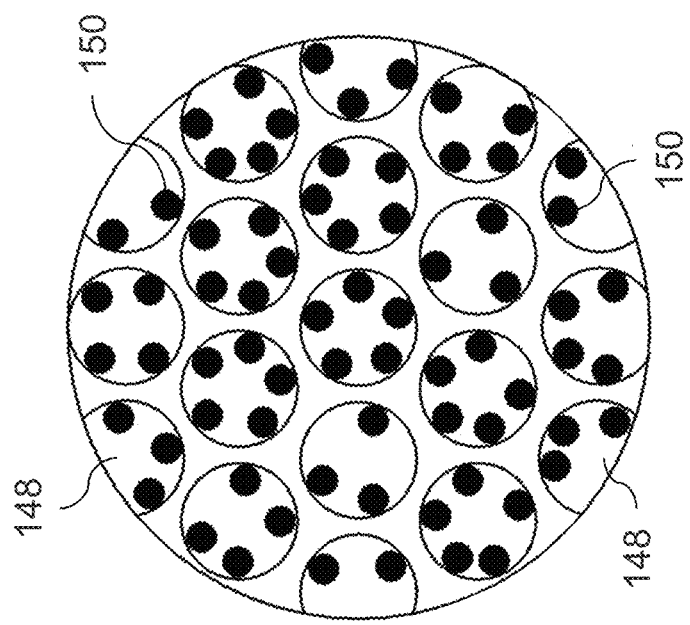
FIG. 4B is an enlarged view of the graphical representation of the sensor of FIG. 4A depicting functionalized metal nanoparticles immobilized in pores.
Figure 4A:
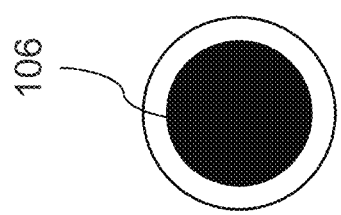
FIG. 4A is graphical representation an enlarged top view of a sensor of FIG. 3.

Turning to FIGS. 4A and 4B, the sensor 106 comprises a nanoporous membrane. Pores 148 of the membrane comprise functionalized metal nanoparticles 150 immobilized on their surfaces. Specifically, the membrane is characterized by nanopores, which are channels 10 nm-1000 nm in diameter and can be up to 200 μm long. For example, the nanoporous membrane may comprise pores that are about 25, 50, 100, 150, 200, 250, 300, 350, 400, 450, and 500 nm in diameter, and about 1, 5, 25, 50, 75, 100, 150 and 200 μm in length.

A sample is flowed through the pores 148 of the membrane, which have relatively small diameters. The relatively small pore diameters, for example about 100 nm, limits the diffusion distance between the chemical targets and their corresponding capture molecules on the nanoparticle surface, thereby reducing the mean diffusion time required for a target chemical to reach a capture molecule. By reducing the diffusion time, the time required for the target-capture molecule system to reach equilibrium may be decreased. The nanoparticles may also be bound to the top and bottom surfaces of the nanoporous membrane.

The working area of a sensor is limited to the width of the coherent light source, which may be approximately 1-4 mm. It is therefore impractical to increase the sensitivity of sensors of the prior art simply by creating a larger planar (two-dimensional) sensor. However, because functionalized nanoparticles are immobilized onto pore surfaces in a three-dimensional membrane, the number of nanoparticles over a given sensor area can be increased with respect to a similar two-dimensional design. In many cases, the number of nanoparticles immobilized within a given sensor area may be increased substantially with respect to a two-dimensional design.

The membrane may be selected to optimize the thickness, pore size, and pore periodicity for a particular chemical sensing application. The diameter of the sensing membrane can be selected based on cost and performance. In an example, the diameter of the sensing membrane may be as small as 1 μm or as large as 13 mm. The light beam size may be close to the diameter of the sensing membrane to maximizing the strength of the absorbance signal. The diameter of the sensor may be small to reduce cost.

Anodized aluminum oxide (AAO) is an example nanoporous membrane material. The dimensions of nanopores in an AAO membrane may be controlled when producing the AAO material. The material is sufficiently optically transparent at LSPR wavelengths to allow for transmission-based spectroscopic measurements to be performed. The transmission of light through the membrane is dependent on several factors including pore size and thickness that impact the absorbance of the membrane material and the scattering it produces in the LSPR wavelengths of interest.

Figure 16:
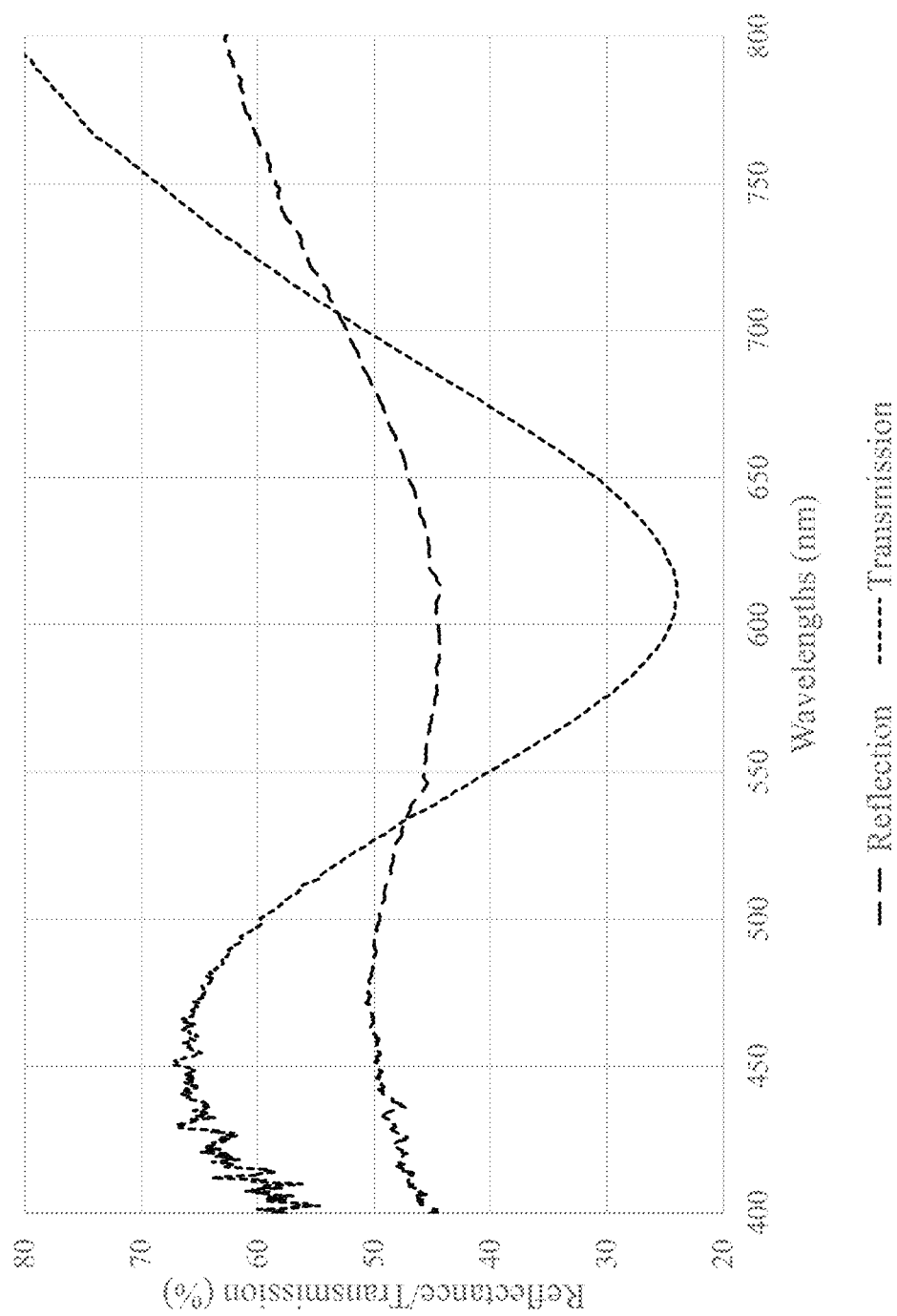
FIG. 16 is a graph showing a comparison of reflection and transmission signal of AAO membrane with 150 nm pores and 50 um thick, with 45 nm gold shell nanoparticles immobilized inside the pores. The LSPR peak is much larger and sharper in the transmission measurement.

Although both reflection and transmission measurements are possible with this system, is has surprisingly been found that transmission measurements provide better results than reflection measurements. In reflectance mode the reflection off of the top surface of the membrane is strong, and accounts for the majority of the signal returning to the detector. This reflected light carries very little nanoparticle absorbance information with it as it is only interacting with the nanoparticles on the top surface of the membrane. In transmission mode, the majority of the light passes through the entire thickness of the membrane before it reaches the detector, interacting with all of the nanoparticles throughout the entire thickness of the membrane. This greatly increases the absorbance component caused by the nanoparticles, increasing the signal to noise ratio and thereby increasing sensor performance. This also ensures that the measured signal is from target binding sites throughout the membrane rather than just those at the top surface. It has further been discovered that a larger proportion of scattering light reaches the detector in reflection mode versus transmission mode, increasing the noise. Also, the AAO pores act as a waveguide, allowing light to propagate within the pores and providing enhanced interaction with the nanoparticles, resulting in unexpectedly high transmission of light with a large LSPR absorbance component, providing further enhancements to the transmission signal which are not obtained when employing reflection signal. FIG. 16 illustrates the dramatic improvement in the LSPR signal when measuring in transmission versus reflection.

However, a transmission system is more difficult to build as the LSPR wavelengths must be matched to the AAO properties to allow sufficient light transmission. Variables such as pore size, and thickness may be tuned depending on the wavelengths used so as not to interfere with the optical signal generated by the immobilized metal nanoparticles. The transmission apparatus can be realized by having a light source on one side of the membrane and a detector on the other side of the membrane. It is also possible to make a pseudo-transmission setup with the light source and detector on the same side of the membrane, if a highly reflective surface is placed beneath the membrane. The reflective surface will cause the transmitted light to travel back through the membrane and to the detector on the opposite side, which is effectively a transmission measurement.

Figure 17:
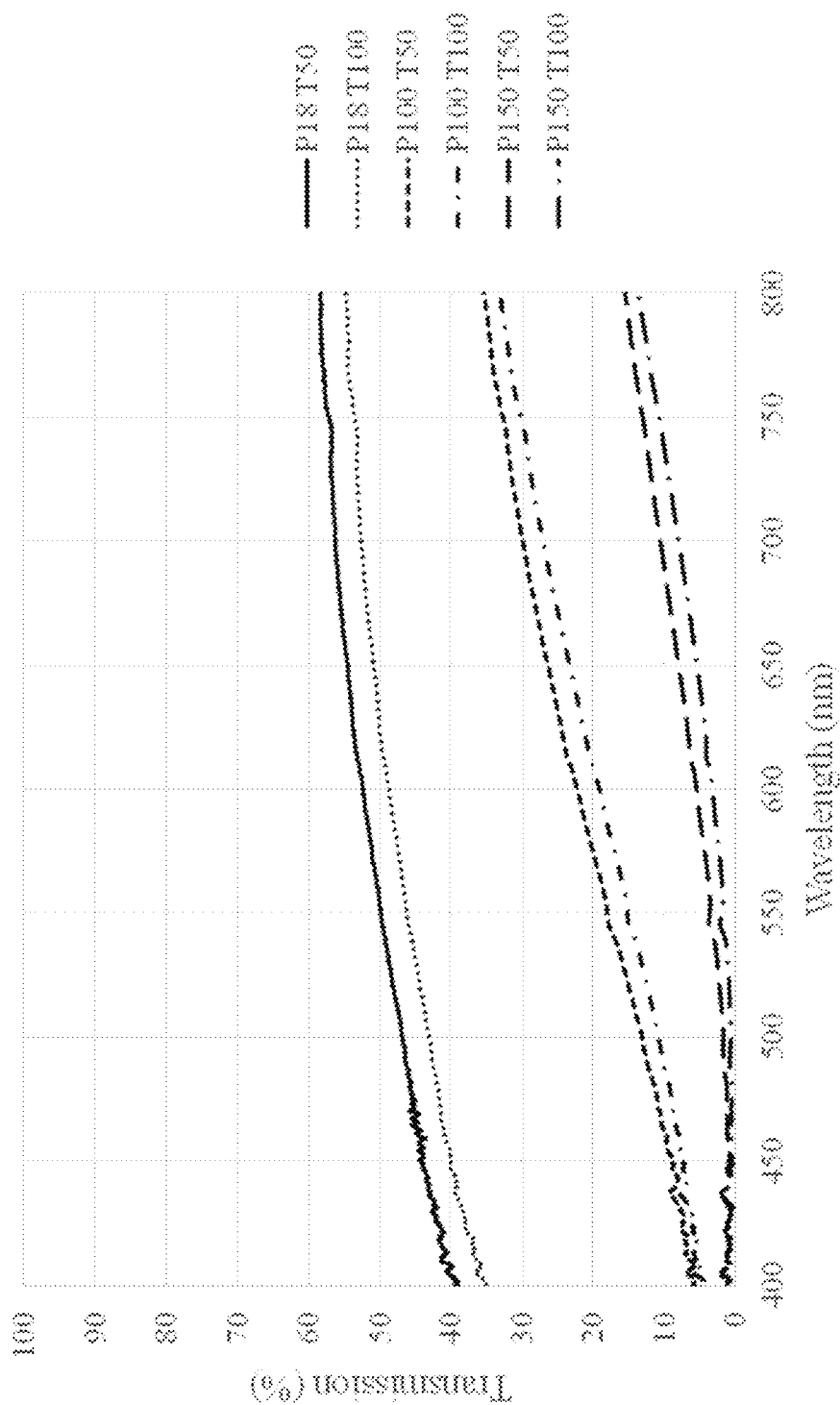
FIG. 17 is graph showing transmission of AAO membranes of various pore size (P, in nm) and thickness (T, in um). Membranes were measured dry in air.
Figure 18:
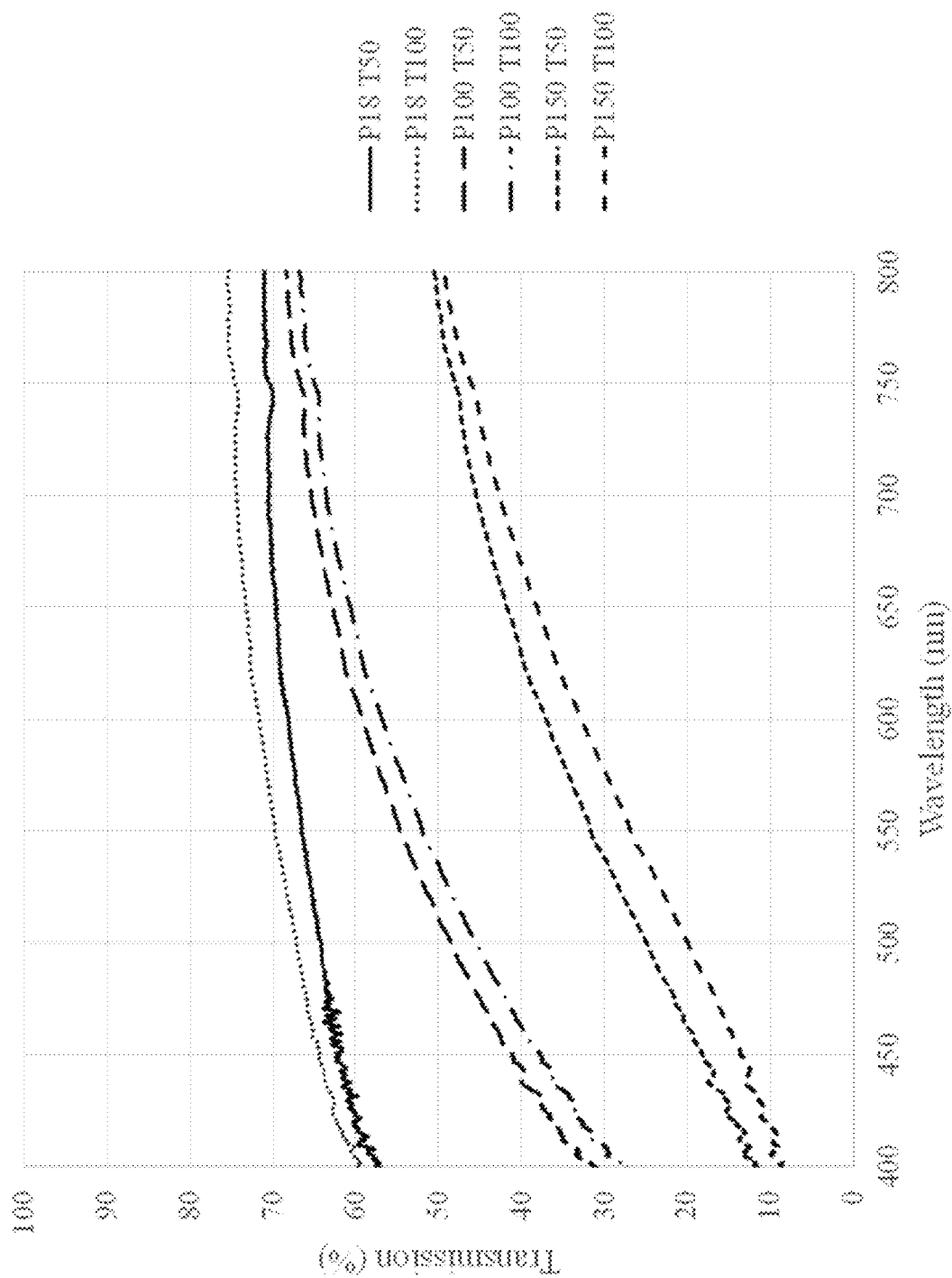
FIG. 18 is a graph transmission of AAO membranes of various pore size (P, in nm) and thickness (T, in um). Membranes were measured wetted with water in air.

In FIG. 17 and FIG. 18, the transmission of various AAO membranes with different pore sizes and thicknesses have been measured both dry and wet with water. In general, smaller pores result in higher transmission compared to larger pores. With respect to thickness, thinner membranes (50 um) have higher transmission compared to thicker membranes (100 um), but the impact is not as significant as pore size. To use AAO as a material in this sensor, the pore size and thickness should be selected to be as small as possible while still allowing the nanoparticles to fit into the pores without blocking them. Now examining the dry vs wet membranes, the transmission through wet membranes is improved, due to refractive index matching, especially for membranes with larger pore sizes (100 and 150 nm). To get the best results, measurements should be taken while the membrane is wet. To further improve the transmission, a high refractive index solution can be introduced after the sample has passed through the sensor. The high refractive index solution will reduce scattering even further, improving the signal to noise ratio.

Any optical signal that is generated by the membrane itself can be removed from spectroscopic measurement by the signal processor 114 using baseline correction methods. A reference measurement of an area of the membrane which is not coated in nanoparticles may be taken to subtract out the optical signature of the membrane using the processor 114, which may enhance the signal produced by the nanoparticles. Pores of a membrane, for example an AAO membrane, can be chemically treated to allow metal nanoparticles 150 to be associated with its surface. For example, the chemicals used to treat AAO include, but are not limited to, polyelectrolytes such as polyallylamine hydrochloride (PAH) and poly-(succinyl-sulphonate) (PSS) that can create a positive or negative electrostatic charge on the AAO surface. Metal nanoparticles stabilized in water by charged surface groups can be associated to the membrane through electrostatic forces. Other methods to immobilize nanoparticles include using a silane based linker, which will covalently bind to the surface of the AAO. For example, a silane-thiol molecule could be used, with the silane covalently binding to the AAO pore wall and the thiol covalently binding to the nanoparticle. The thiol could be replaced with any chemical group that associates to the nanoparticle surface, such as an amine group, for example. The AAO may be pretreated to generate hydroxyl groups on the surface of the pores to promote silanization, through a procedure such as incubation in a 1:1 solution of hydrochloric acid and methanol for 30 minutes, or any other method that can be used to generate hydroxyl groups the surface.

It will be appreciated that various other nanoporous membrane materials may be used including various organic and inorganic membranes that are at least partially transparent at the LSPR wavelengths of interest. Advantageously, metal nanoparticles may be associated directly to these membranes if the membranes contain thiol-, amide-, phospho- or other functional groups.

The membrane material could also be chemically treated with polyelectrolytes such as PAH, PSS or other charged polymers to associate the metal nanoparticles to the surface through electrostatic interactions. Reaction chemistry such as N-Hydroxysuccinimide/ethyl(dimethylaminopropyl) carbodiimide (NHS/EDC) coupling among other coupling chemistries may also be used to bind the metal nanoparticles to the surface. It will be appreciated that there exist other methods of immobilizing functionalized metal nanoparticles 150 to an optically transparent nanoporous material.

Turning now to FIG. 4C, an example of functionalized metal nanoparticles 150 functionalized to a pore surface of an AAO membrane is provided. The AAO membrane 154 has a bilayer of charged polyelectrolyte 156 on its surface that facilitates the association of charged metal nanoparticles 150 to the walls of the pores.

The metal nanoparticles shown in the example of FIG. 4C have two different metal core shapes, a sphere 160 and a rod 162, which may be used together or independently. Both are functionalized with antibodies 164 as the capture molecule with their distinctive Y-shape and form a self-assembled monolayer (SAM) on the surface of the nanoparticle. Blocking molecules 166 prevent non-specific binding to empty binding sites on the metal surface. The capture molecules may also comprise aptamers, polymers, or DNA The SAMs may comprise an antibody, aptamer, polymer, DNA or other capture molecule that is bound to the nanoparticle 150 surface and capable of selectively binding to the chemical of interest. In the case of gold nanoparticles, this binding typically occurs spontaneously between the gold surface and thiol groups that are natural to the capture molecule or have been chemically added to the capture molecule or nanoparticle surface.

To prevent non-specific binding of non-target chemicals, inert blocking molecules are used to pacify empty binding locations on the nanoparticle and pore surfaces. Blocking molecules for metal nanoparticles may comprise thiolated compounds with inert end groups that provide aqueous stability such as carboxyl, methyl, or polyethylene glycol (PEG). For the pores, blocking molecules may be silane based compounds with inert end groups such as carboxyl, methyl, or PEG. Bovine serum albumin (BSA) is another example of a possible blocking molecule that may be used on nanoparticle and pore surfaces. Together, the capture and blocking molecules form a SAM that imparts functionality onto the metal nanoparticle.

To create a functional sensor 106, the metal nanoparticles are first immobilized on the nanoporous membrane surface then the nanoparticle is functionalized with a SAM. Alternatively, the particle may first be functionalized with a SAM and the nanoparticles may be immobilized on the membrane.

The size, shape and elemental composition of metal particles affect the location and intensity of the LSPR absorbance peak in the electromagnetic spectrum. As such, the size, shape, and composition of nanoparticles are selected to allow for a measureable transmission signal through the nanoporous membrane. The size and shape of the nanoparticles are also selected to avoid physical clogging of the pores of the selected sensor membrane.

Various metal nanoparticles have different bulk refractive index sensitivities and electromagnetic decay lengths, which may be tuned to produce the optimal LSPR sensor response for a given capture-target system. Decay length and sensitivity are typically not independent parameters, and both can be tuned with the size, shape, and composition of the nanoparticle. For example, increasing the size of a spherical nanoparticle increases both the sensitivity and the decay length. Other nanoparticle shapes may have different trends with respect to size, sensitivity, and decay length. Preferably, a nanoparticle will have the highest sensitivity with a decay length that is similar to the thickness of the capture molecule-target complex. For example if the total size of the capture molecule-target complex is 8 nm, the optimal decay length would be near 8 nm. As such, the size, shape, and composition of the nanoparticle can be tuned based on the sensitivity and decay length parameters for a particular capture molecule-target complex. This also must correspond with the necessary optical properties to allow sufficient transmission of the LSPR signal through the membrane.

Therefore the nanoparticles can be selected depending on the one or more specific chemical target being investigated by the sensor 106.

Compositions of metal nanoparticles that can be used for LSPR include gold, silver, platinum, gold coated silver, silver coated gold, combinations of these metals, and others. The shape of the nanoparticles used can also vary. Useful nanoparticle shapes include but are not limited to, rods, stars, urchins, decahedra, hexagons, triangles, shells, prisms, platelets, spheres, rice, plates, cubes, cages, stars and bipyramids. The dimensions of the metal nanoparticles can range between about 1 nm and 1000 nm with a variety of area to volume ratios.

Figure 4D:
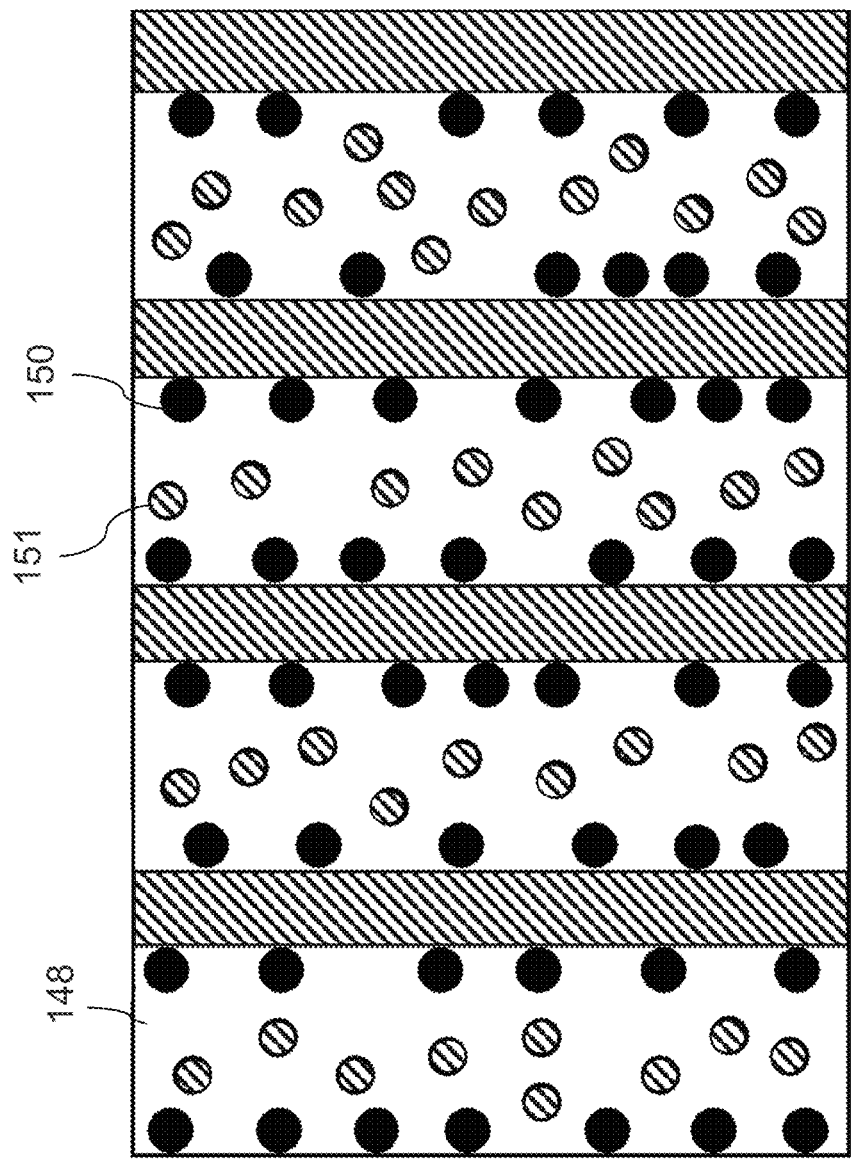
FIG. 4D is another enlarged view of a pore depicting various types of functionalized metal nanoparticles immobilized the pore.

Referring now to both of FIGS. 4C and 4D, a combination of two or more types of nanoparticles may be immobilized on the surface of a single membrane. Each of the nanoparticle types may have been functionalized with a specific capture molecule. For example, nanoparticle 150 may be functionalized with capture molecules to capture a first target chemical whereas nanoparticle 151 may be functionalized with capture molecules to capture a second target chemical.

Figure 19:
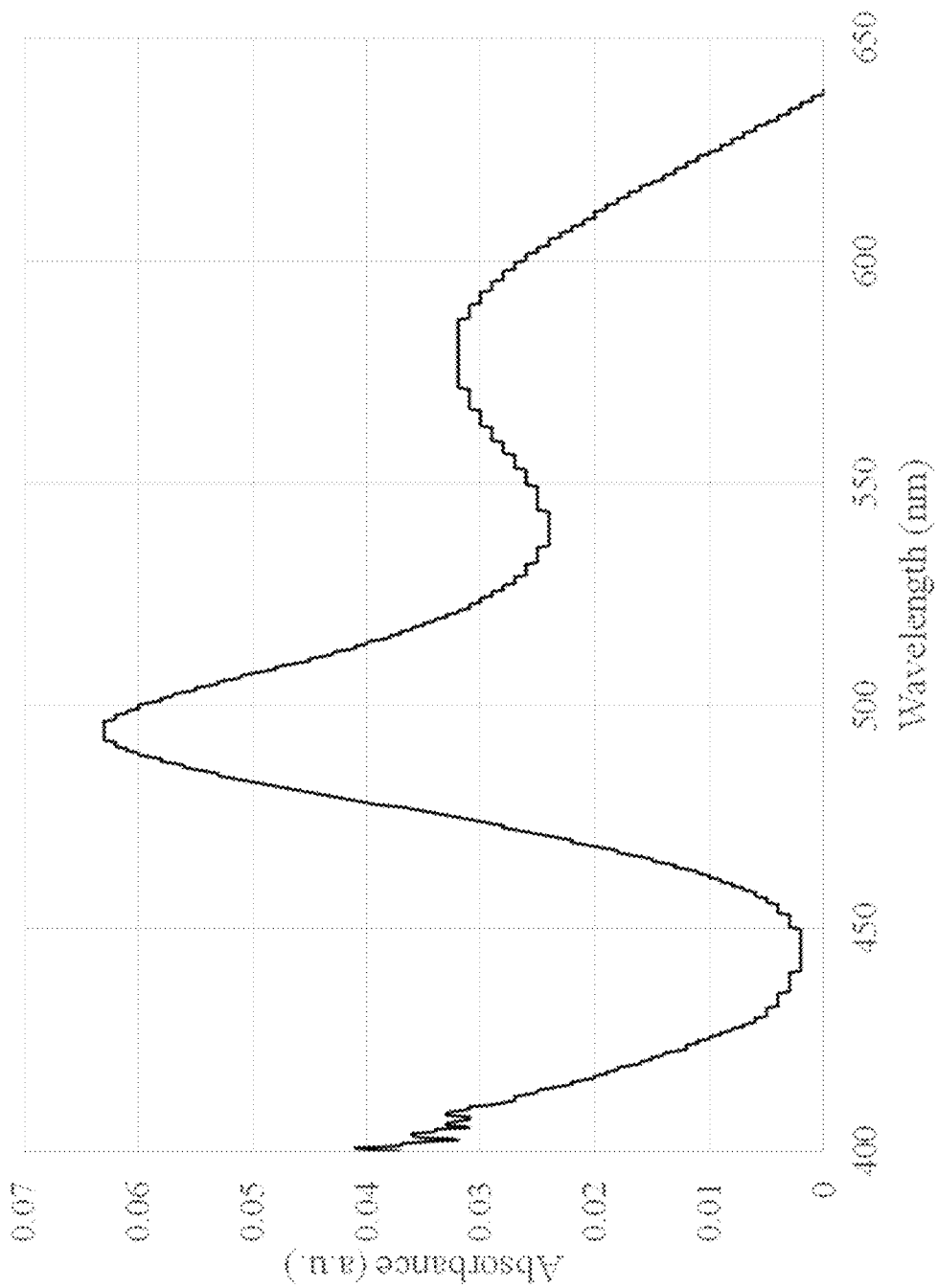
FIG. 19 is an absorbance spectrum of an AAO membrane containing nanoparticles with two different LSPR peak positions, one located at approximately 495 nm and the other at approximately 580 nm.

With a combination of different nanoparticles (shapes, sizes and/or metals) functionalized to capture different targets, antibodies on the spherical nanoparticle may be selective to different targets from antibodies on the rod nanoparticle, each nanoparticle producing a distinct signal. Therefore, the concentration of each target can be determined from a single absorbance spectrum if the spectrum from each of the different particles does not overlap to such a degree that deconvolution of the peaks is impossible. Various particles are used to allow the detection of multiple targets on a single membrane. FIG. 19 shows two different particles immobilized in the same membrane, one with a resonance at approximately 495 nm and the other with a resonance at approximately 580 nm. The two peaks are clearly distinguishable and can be used for generating two independent signals from a single sensor. Any combination and any number of nanoparticles with different LSPR peak positions may be used to achieve multiple measurements. The incorporation of multiple particles with different LSPR peak positions within a membrane allows for a higher density of each particle to be present compared to the case if multiple particles were incorporated onto a planar substrate. Higher particle densities may offer better sensor performance due to high signal to noise ratios. This system may allow detection of multiple target using a small initial sample which may be very advantageous in the case where sample is limited or difficult to obtain. Detecting multiple targets in tandem may also speed the time to obtaining results.

Various particles could also be attached to distinct areas of the same membrane using a tool similar to a protein spotter or various microchannels to allow geometrical separation of the particles. This is advantageous if using a photodetector rather than a spectrometer, or if cross reactions may occur between particles due to their chemically modified surfaces. The use of different particles on a single membrane can also facilitate the use of a control sensor to compensate for errors induced by non-specific binding, temperature change, bulk refractive index change, or other factors. This could be achieved by functionalizing one nanoparticle with a capture molecule and blocking molecule, and functionalizing a second particle with only a blocking molecule similar to the blocking molecules used in the first nanoparticle. Any peak changes that are detected from the second nanoparticle are erroneous, and as such, the second nanoparticle acts as a control. The different nanoparticles may be spectrally distinct or geometrically distinct.

Nanoparticles are immobilized onto the membrane walls through contact between the walls and a colloidal nanoparticle mixture. To permeate the nanoparticles throughout pores of the membrane, a variety of techniques may be employed. The nanoparticles may be physically pumped through the membrane, they can be driven into the membrane through the use of electrical potential, and they could enter by diffusion among, other methods.

Figure 22:
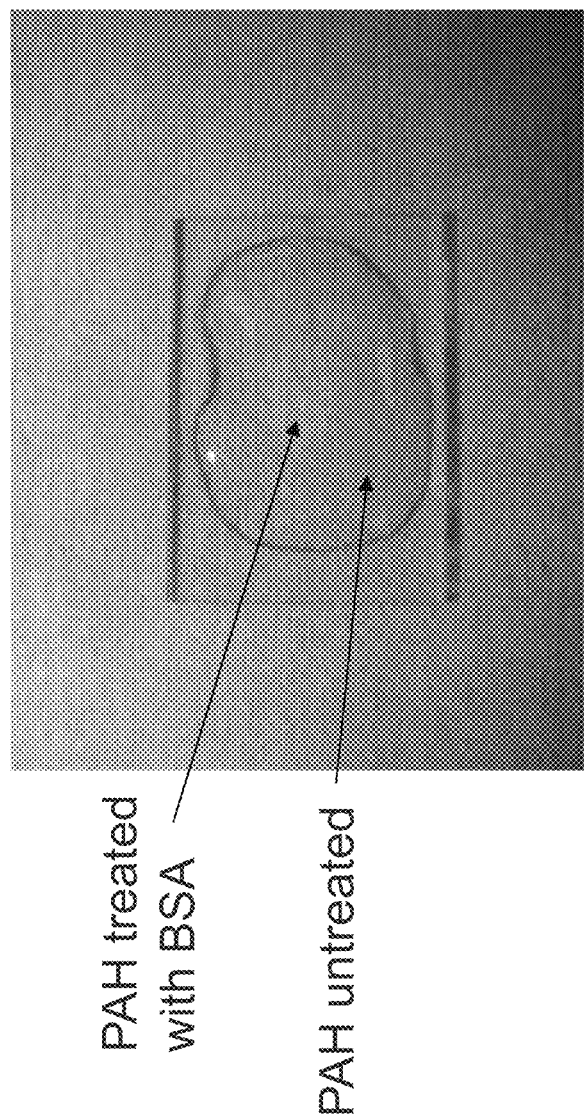
FIG. 22 shows that BSA prevents nanoparticles from binding to a PAH treated surface, on a glass slide

The metal nanoparticles must remain relatively dispersed while immobilized in the pores, as extensive aggregation will affect the quality of the measurements due to peak broadening or pore clogging. It has been discovered that in order to improve the penetration and dispersion of the nanoparticles throughout the membrane pores, surface stabilizing additives can be included in the colloidal nanoparticle mixture. Alternatively, or in addition, the additives may be applied before the nanoparticles are immobilized on the membrane by pumping or incubating the additives through the membrane before the colloidal nanoparticle mixture is applied. It has been discovered that surface blocking additives are especially important in order to immobilize large nanoparticles into small pores. For example, AAO membranes with 100 nm pores were treated with PSS then PAH to render the surface positively charged. Gold nanoparticles 20 nm in diameter and coated in negatively charged citrate were pumped through the PSS/PAH coated membrane. No gold particles were observed to bind to the AAO pores. Upon addition of 0.01% BSA to the 20 nm gold colloidal solution and pumping through the membrane, gold nanoparticle binding was observed on the AAO pores. It is hypothesized that the zwitterionic nature of BSA acts to help stabilize the nanoparticles, possibly by screening the charges at the top surface of the AAO membrane, allowing the nanoparticles to more easily enter and travel through the membrane. In another experiment, a PSS/PAH modified 150 nm AAO membrane was dipped into a 1% BSA solution and rinsed with water. A 20 nm gold colloidal solution, without any BSA additive, was pumped through the membrane, and nanoparticle binding was observed. Binding was observed in the pores at a high density, with a low density of binding on the membrane surface. Increasing the BSA dip concentration to 10% caused a reduction in the binding density of the nanoparticles within the pores, with almost no nanoparticles present on the surface of the membrane. A control experiment was done on glass with a coating of PAH. BSA at 0.01% was incubated in a small droplet on the surface of the glass and rinsed away. A 20 nm gold colloid solution was then applied to the glass. Nanoparticle binding was observed to occur in areas in which there was no BSA, demonstrating that BSA may prevent the nanoparticles from binding to the PAH treated surface. This is shown in FIG. 22. A final experiment was performed with a PSS/PAH modified 150 nm membrane dipped in 1% BSA. 0.001% BSA was added to the gold colloid solution and pumped through the membrane. Binding was observed in the pores and on the surface but at a lower density than without the BSA additive. BSA, acting as a surface blocker, can be used to reduce membrane surface binding, helping to prevent agglomeration. BSA can also act as a stabilizer, allowing larger particles to more easily enter smaller pores. As we have demonstrated, smaller pore sizes are more transparent and so may be preferable to use. Also, larger nanoparticles have higher sensitivities, so they may also be preferable to use. So the use of surface stabilizing additives may allow a better sensor to be fabricated. Other possible additives include various inorganic salts, various surfactants such as Tween 20 or Triton X, or PEG, along with a variety of other potential molecules and combinations. It is also assumed that these additives will have similar effects when other nanoparticle binding methods are used other than charge interactions based on PSS/PAH, such as covalent methods using thiol chemistry as described previously.

The nanoparticles may be functionalized with capture molecules before or after they are immobilized on the pore walls. If they are immobilized prior to being functionalized, they can be immobilized on the pore walls through electrostatic interactions or using functional groups bound to the membrane that would be capable of binding to the nanoparticles, for example, in the case of a gold surface of a nanoparticle a thiolated polymer may be used. If the nanoparticles are functionalized prior to being immobilized, as they may be in the case of a multiplexed sensor, for example, a functional group would be used.

Alternatively, nanoparticles 150 and 151 may be functionalized to capture the same target chemical and any difference in signal could be used to generate a baseline signal, thereby removing uncertainty in the signal.

Figure 5:
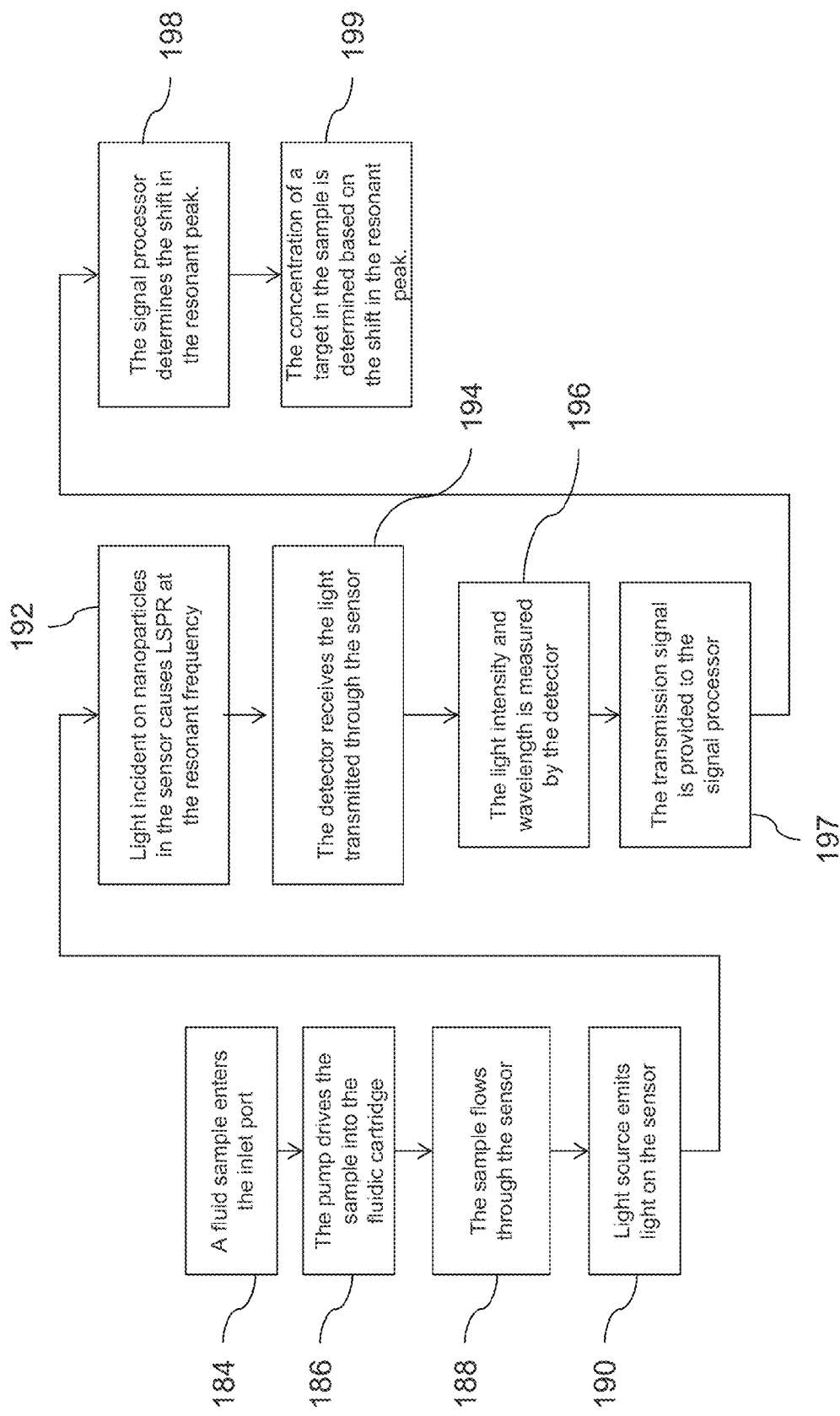
FIG. 5 is an process flow diagram outlining an example for obtaining a reading from the chemical-sensing system of FIG. 1.

Turning to FIG. 5, an example process for sampling a fluid is provided. In step 184, a sample fluid enters the inlet port 102. In 186, the pump 112 drives the sample into the fluidic cartridge 104 and the sample flows through the sensor 106 in step 188. In step 190, the light source 108 emits light onto the sensor 106 in the fluidic cartridge 104, which causes LSPR interactions in 192. In 194, the detector receives light transmitted though the sensor 106, measures the light intensity and wavelength in 196 and generates a transmission signal in 197. In 198, the signal processor 114 determines whether a shift in the resonant peak is observed and in 199, detects the presence and/or determines the concentration of the target chemical in the sample based on the resonant peak shift, as described above.

Figure 6:
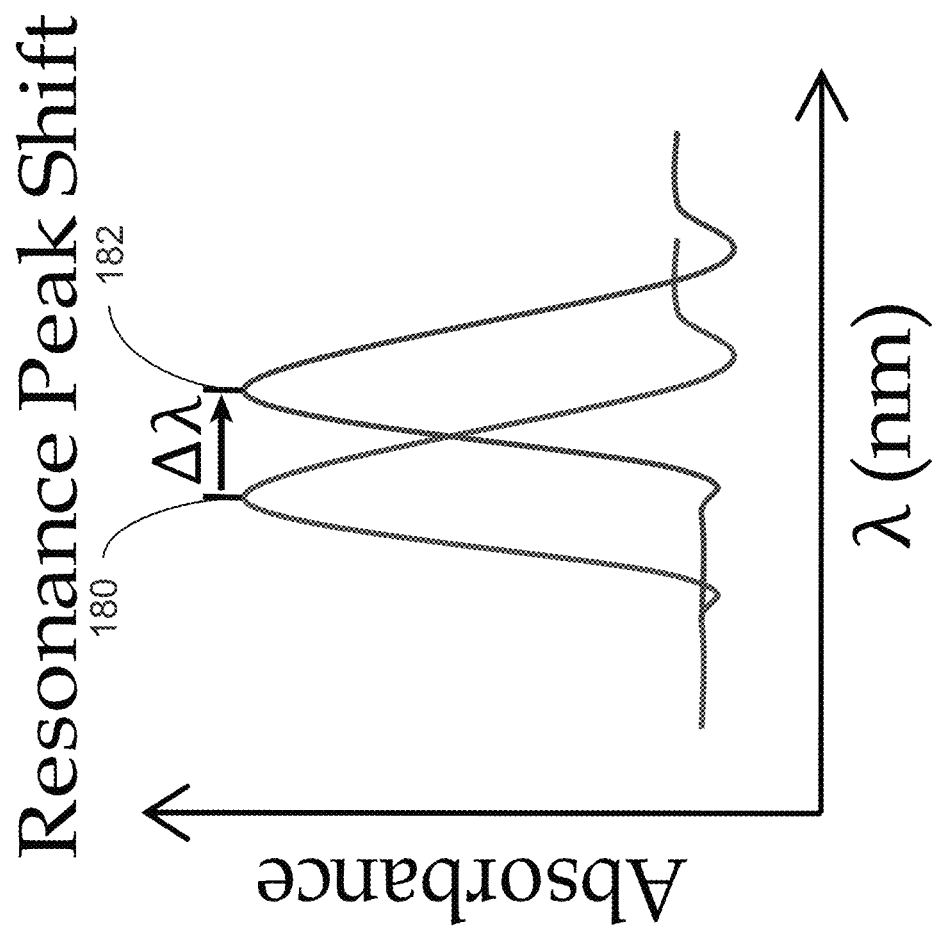
FIG. 6 is a plot showing the resonance peak shift due to binding of the target chemical with capture molecules on a sensor.

Referring now to FIG. 6, the change in peak position or intensity induced by binding of the target chemical to the capture probe can be monitored in real time or by comparing the peak position prior to the target chemicals binding to the capture molecules in the sensor 106 with the peak position after the target chemical has bound to the capture molecules in the sensor 106. This binding may be referred to as a binding event.

The change in peak position can be compared to data obtained from a standard curve of peak change vs. concentration by the signal processor 114, and using a fitting algorithm the presence of a target chemical in a sample may be detected, and the concentration of the target in the sample may be determined, by the signal processor 114. Alternatively, or in addition, the rate of change (the slope) of the signal may be used to more rapidly determine the concentration by comparing the calculated slope to data obtained from a standard curve of slope vs. concentration. Various data processing mechanisms may be employed by the signal processor 114 during data collection to improve the signal to noise ratio of the optical signal, such as smoothing and averaging functions. High speed acquisition is used to facilitate real time averaging and smoothing. Various peak fitting algorithms may be employed that offer a high level of stability in the peak position.

An indication of whether a target chemical was detected may be output by the signal processor 114. The indication may be output, by way of example, on a display, as an indicator light, as a warning signal, or as an electronic message. Alternatively, or in addition to the indication, the concentration of the target chemical may be output by the signal processor 114 or on a display linked to the signal processor such as the display of a cellular phone. Results of assays can be stored in built in memory on the device, on peripheral devices, or stored in a cloud-based server.

The spectrometric optical measurements taken through the membrane expose the surface area of the membrane and all of the particles contained therein, and hence, the sensor may be referred to as a three-dimensional sensor. A single sensor 106 may be adapted to detect multiple targets within a single fluid sample through the inclusion of multiple membranes or functionalized particles with different shapes, sizes or metals.

Figure 7:
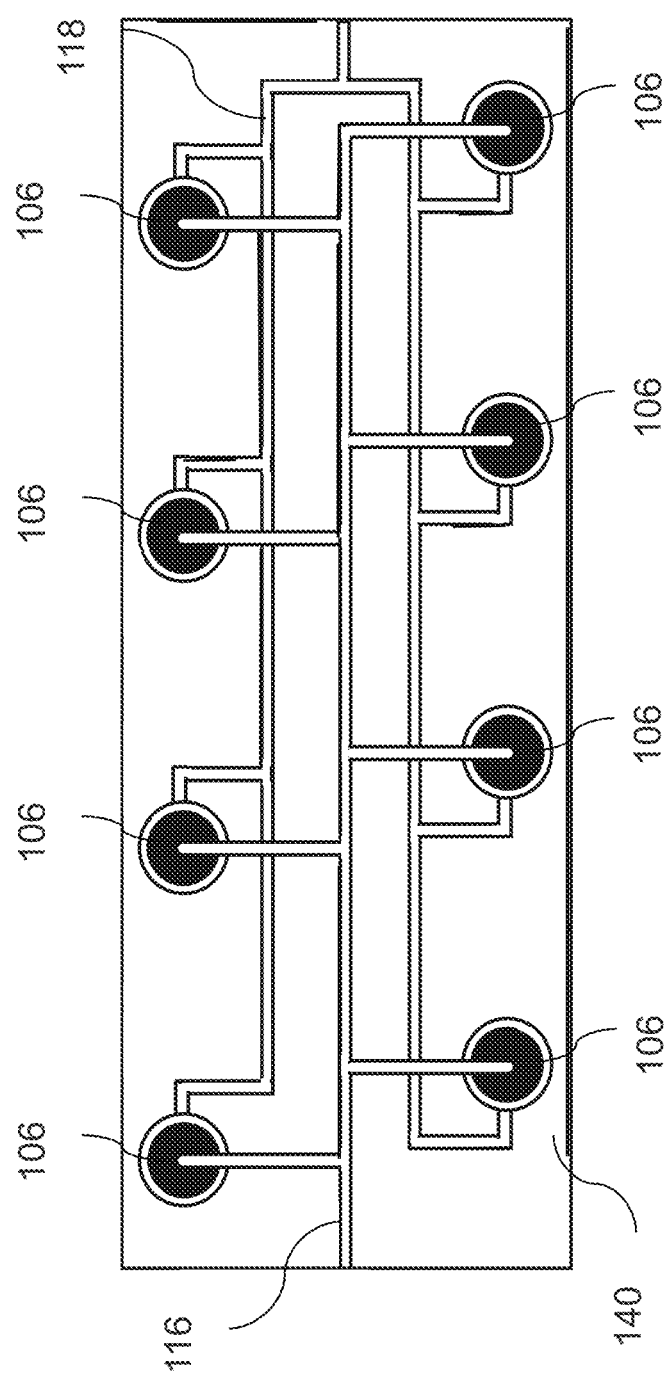
FIG. 7 is an overhead view of a fluidic cartridge similar to that of FIG. 3 comprising multiple sensors.

A multiplexed design for the fluidic cartridge is provided in FIG. 7. The inlet 116 is split and leads through several independent sensors 106, which are fluidically connected to the outlet 118. The sensors 106 are oriented to allow light transmission and spectrometric measurement. A multiplexed design can also be achieved using several fluidic microchannels coming from a single channel that carry the sample through different areas of the same membrane that have been functionalized for the same or different targets.

Multiplexed measurements can be taken with multiple light sources and spectrometers (or other light measurement mechanisms such as a photodetector), a multiplexed spectrometer such as a hyperspectral imager, or by moving the chip to align each sensor under a single light source using the chemical sensing system 100 shown in FIG. 1. The flow through a multiplexed fluidic cartridge may be controlled by a single pump 112, however, designs that employ multiple pumps or other components to facilitate flow may also be used.

Figure 8:
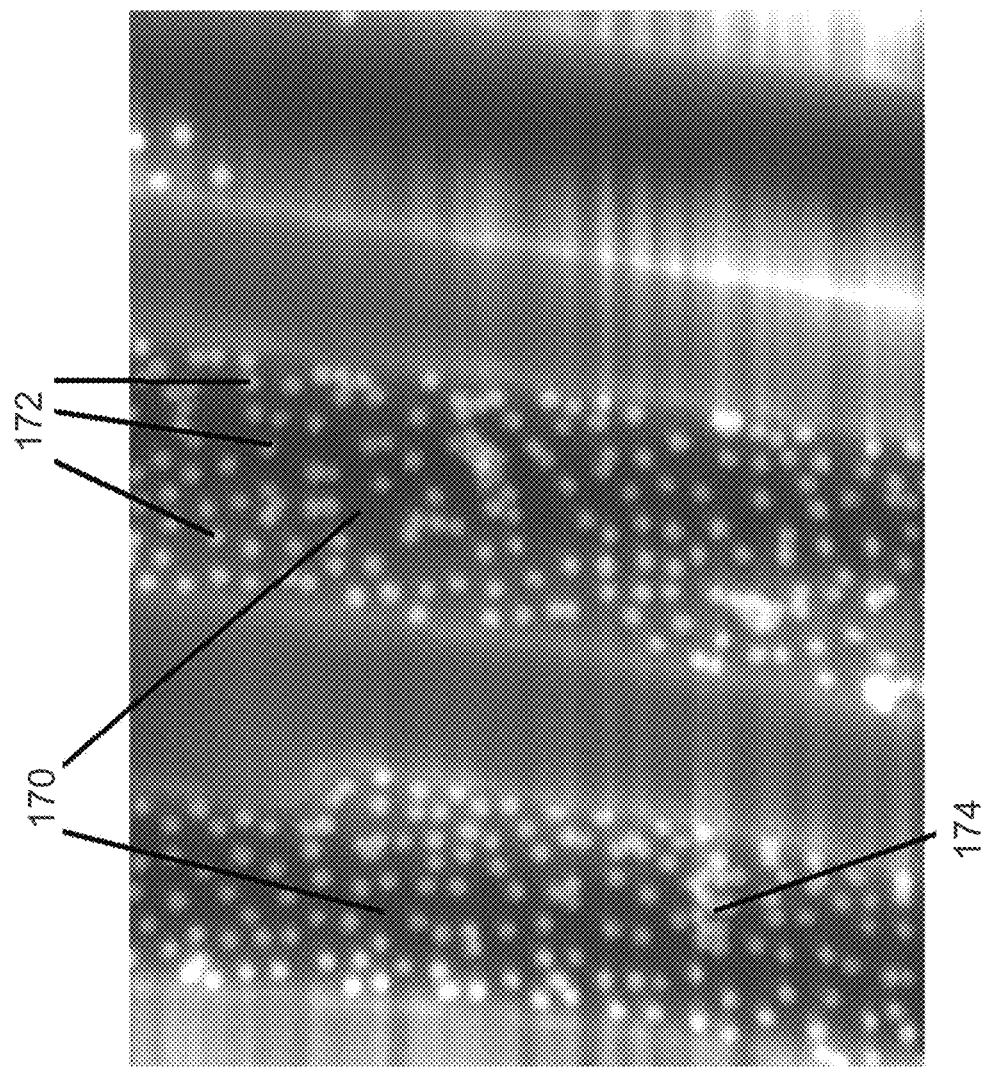
FIG. 8 is scanning electron microscope (SEM) image of 20 nm gold nanoparticles immobilized on an anodized aluminum oxide (AAO) membrane with a 200 nm pore diameter.

FIG. 8 is a scanning electron microscope (SEM) image of 20 nm gold nanoparticles 172 immobilized in the pores 170 of a 200 nm pore size AAO membrane. This figure demonstrates that the metal nanoparticles 172 may be immobilized throughout the pores 170 in a substantially dispersed manner. An agglomeration 174 is also shown on the surface of the pore 170 which may result if surface stabilizing additives are not employed.

Figures 9A, 9B:
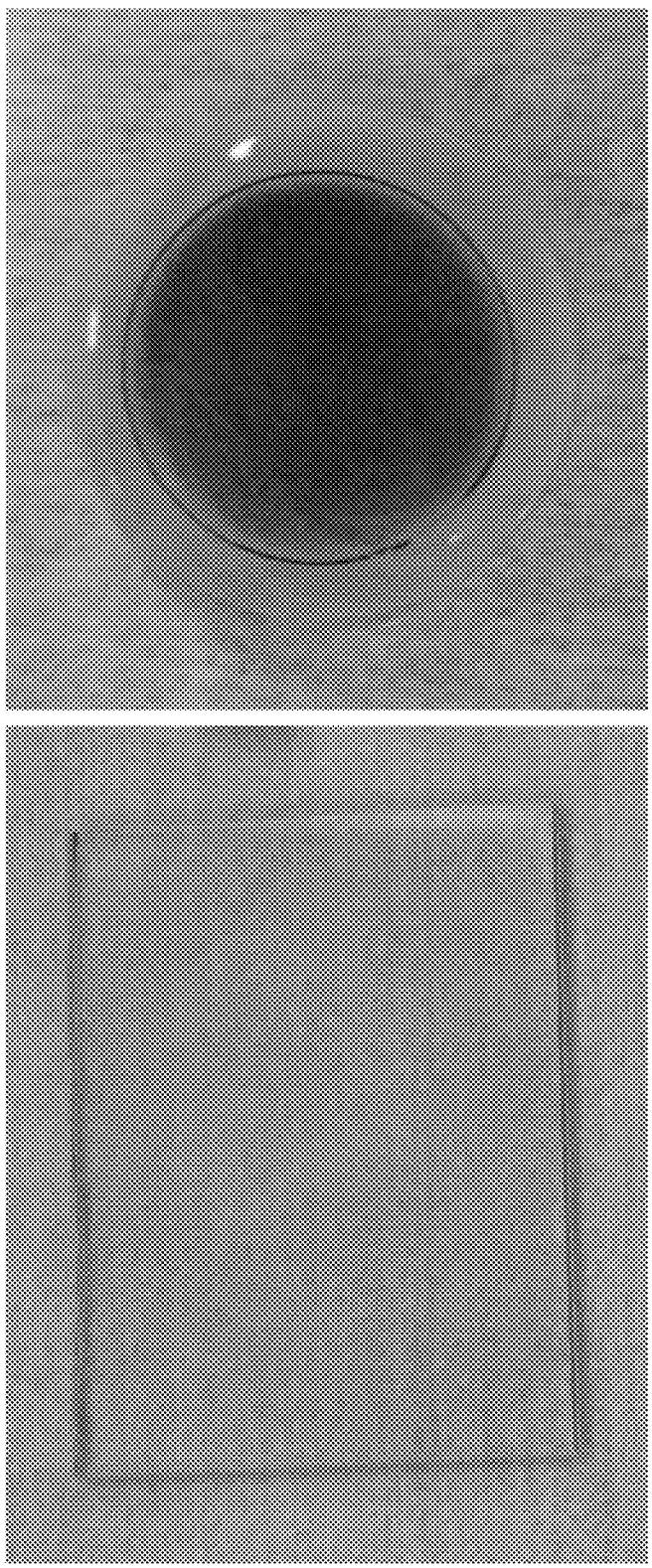
FIG. 9A is a photograph of gold nanoparticles (GNP) immobilized on a glass slide.
FIG. 9B is a photograph of gold nanoparticles immobilized on an AAO membrane.

FIGS. 9A and 9B, 10, 11, 16, 20, and 21 illustrate advantages of an example three-dimensional AAO membrane in comparison with conventional two-dimensional sensors. The glass slide of FIG. 9A comprises gold nanoparticles immobilized onto its surface. In contrast, the membrane of FIG. 9B is an AAO membrane comprising gold nanoparticles immobilized on the surface throughout its pores. The red appearance of both images is due to the LSPR of the immobilized gold nanoparticles. The AAO membrane appears as a very dark red in comparison to the glass slide due to the larger number of immobilized gold particles per given unit of sensor surface area. Therefore, for each given unit of surface area, there is a stronger LSPR interaction due to the greater number of immobilized nanoparticles.

Figure 10:
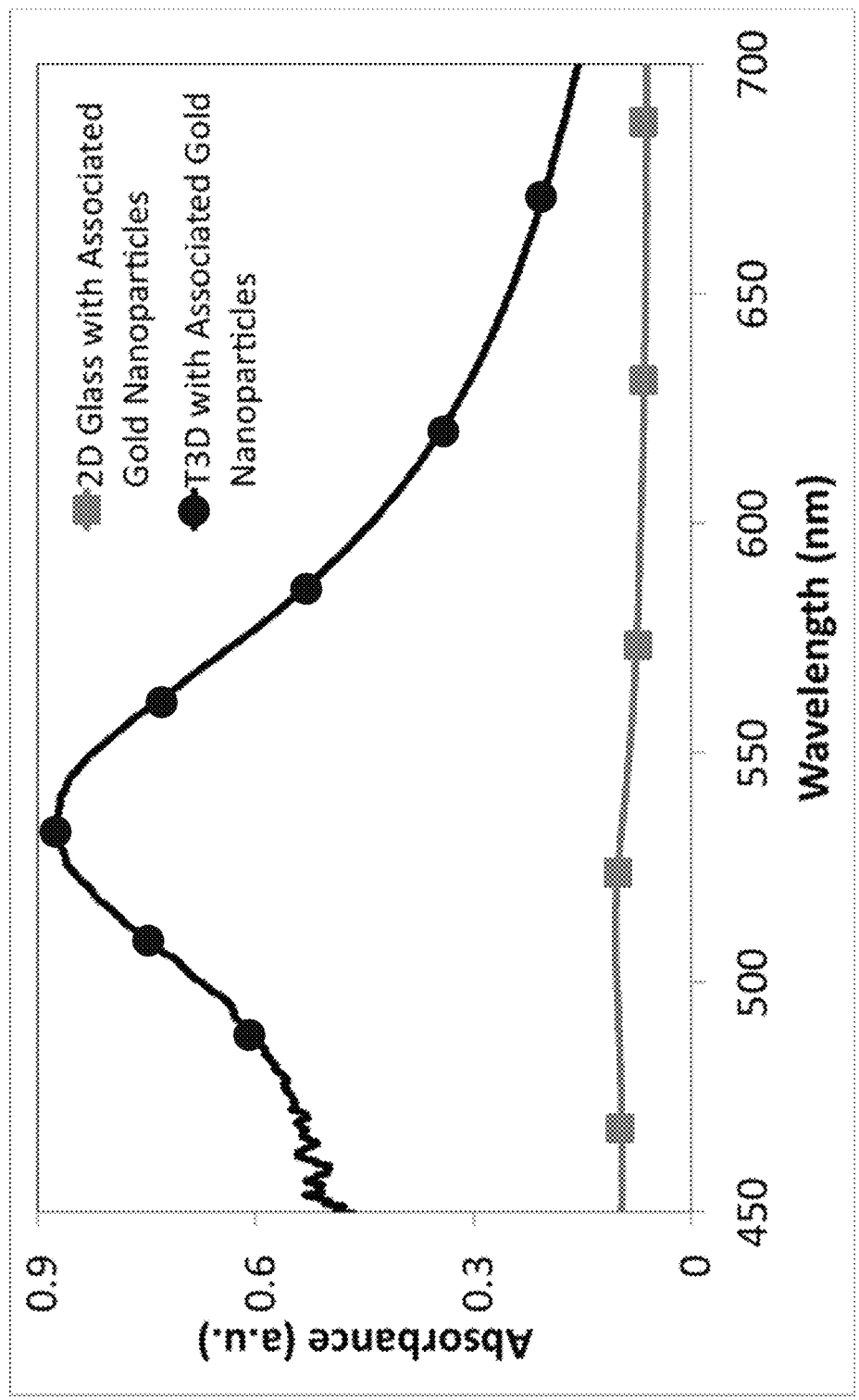
FIG. 10 is an example plot showing the relationship between absorbance and wavelength for an AAO membrane having gold nanoparticles immobilized in its pores with respect to a glass slide having gold nanoparticles immobilized on its surface.

FIG. 10 is a chart of the absorbance spectrums of the glass slide with respect to the AAO membrane of FIGS. 9A and 9B, respectively, taken in absorbance mode. The absorbance peak of the AAO membrane is approximately 6 times larger than the glass slide absorbance peak, which demonstrates that an AAO membrane may accommodate a higher number of gold nanoparticles, and therefore, may accommodate a higher number of accessible capture molecules with respect to a planar glass slide.

Figure 11:
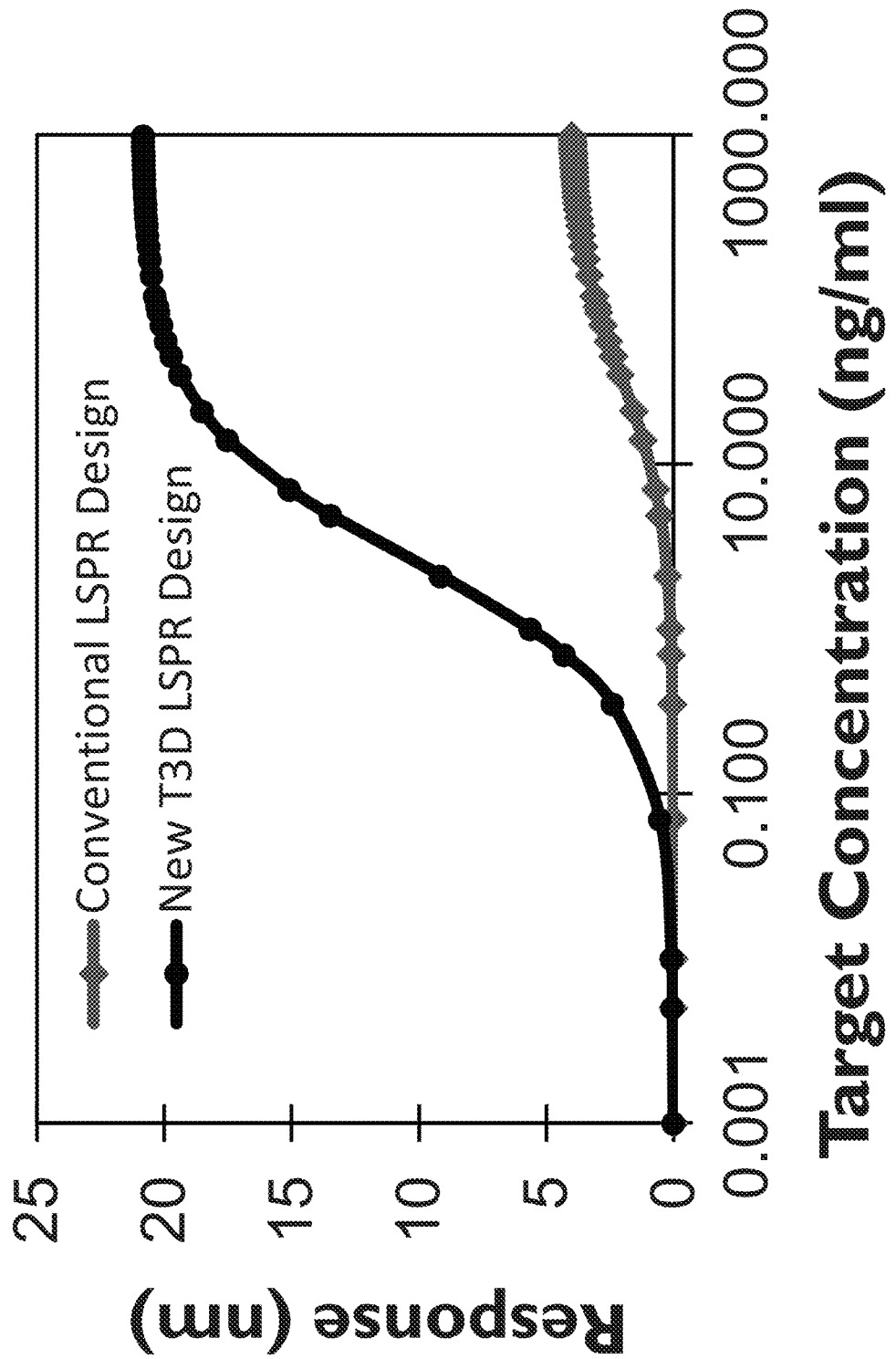
FIG. 11 is an example plot showing resonance peak shift with respect to target concentration in a solution.

FIG. 11 is a plot showing the simulated response of a sensor based on a glass slide (the conventional LSPR design) with respect to a sensor based on an AAO membrane, which may also be referred to herein as a transmissive three-dimensional (T3D) LSPR design (New T3D LSPR Design). Although not directly visible from the plot of FIG. 11, the detection limit of the sensor comprising the AAO membrane at (2 pg/ml) has been predicted by computer simulations to be improved by approximately 1000 times when compared with the 2D arrangement (2000 pg/ml).

Figure 12:
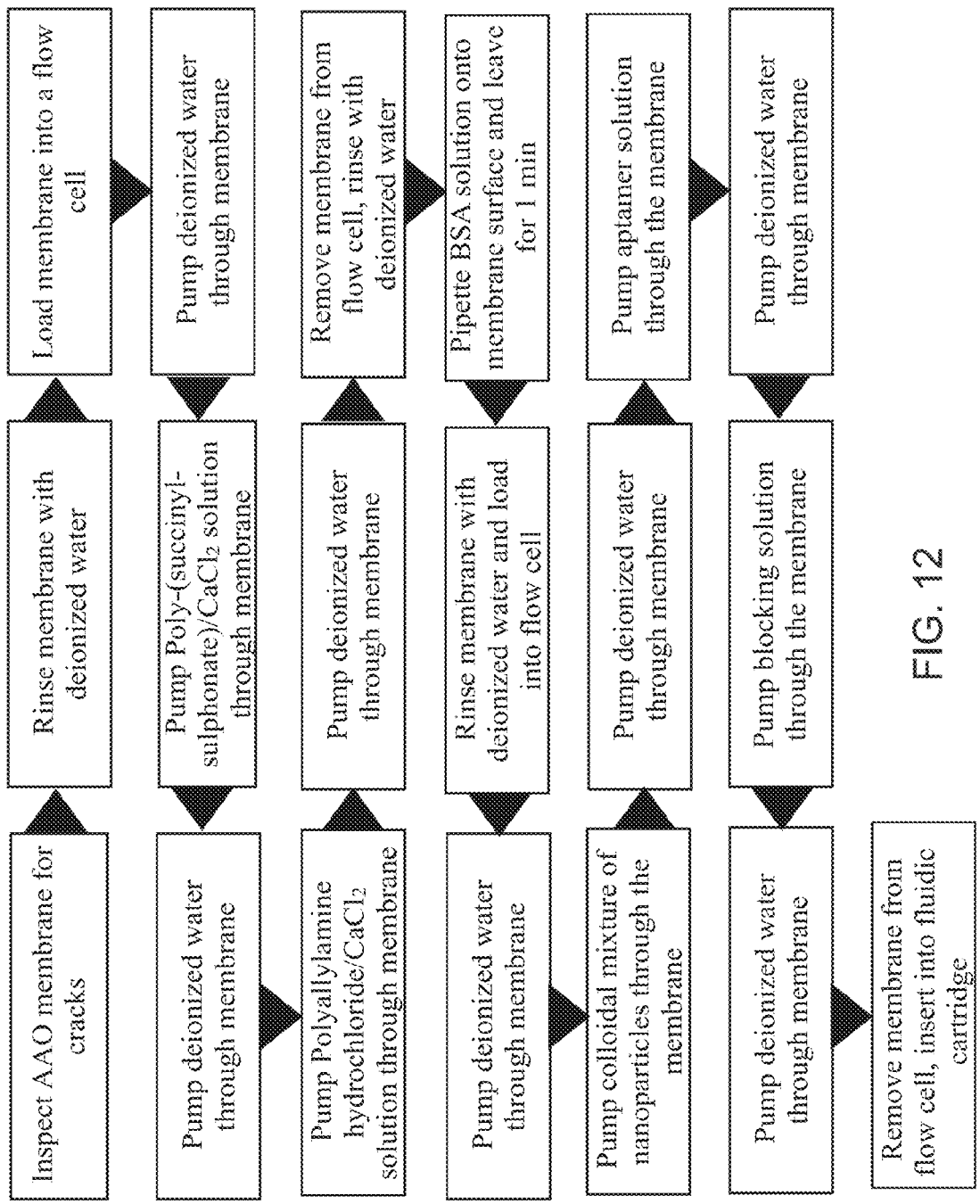
FIG. 12 is a process flow diagram of an example process for GNP immobilization on the pores of an AAO substrate and subsequent functionalization with capture molecules and blocking molecules.
Figure 13:
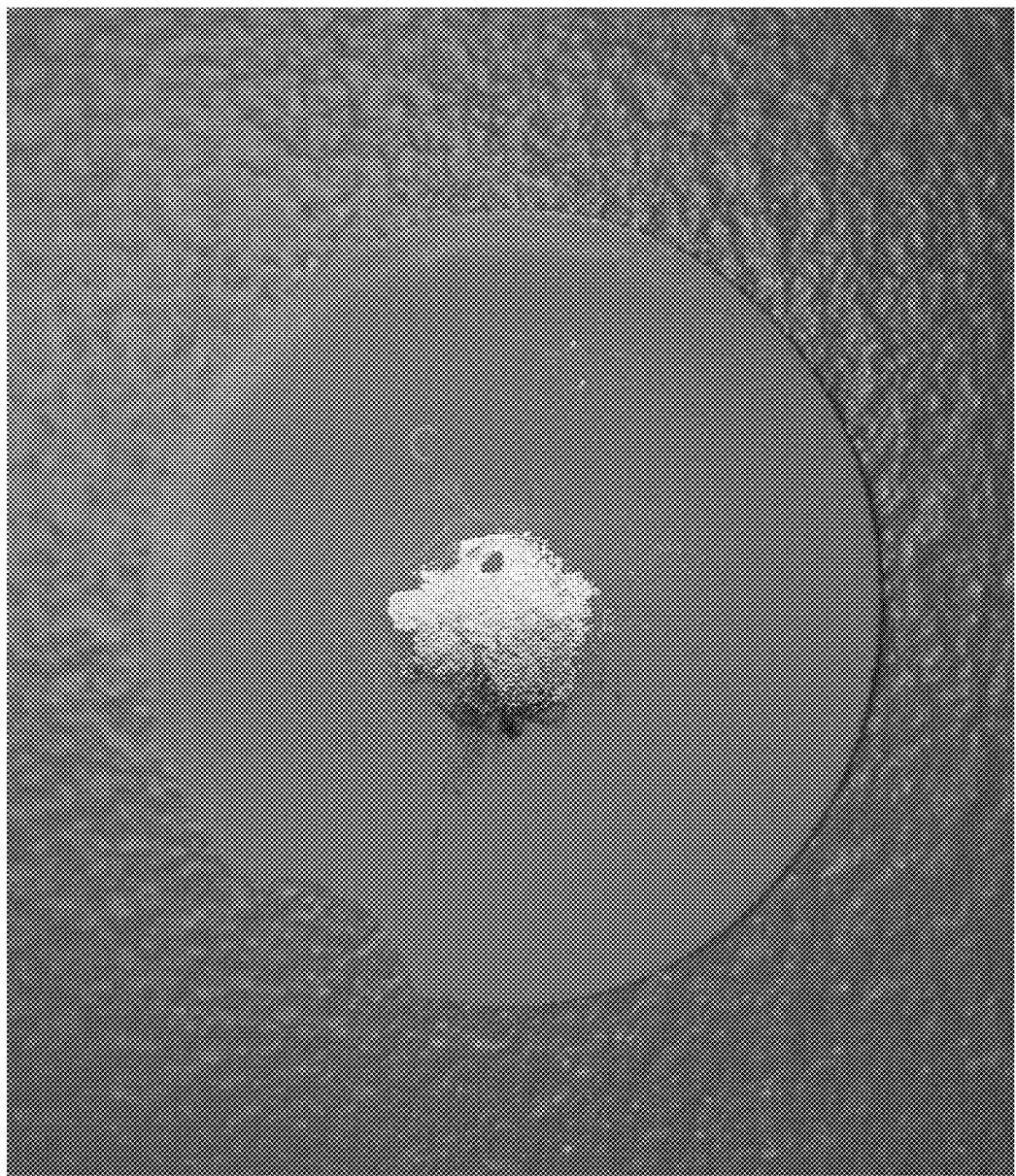
FIG. 13 is an image of AAO membrane with gold nanoparticles immobilized thereon without the use of BSA additive or coating.
Figure 14:
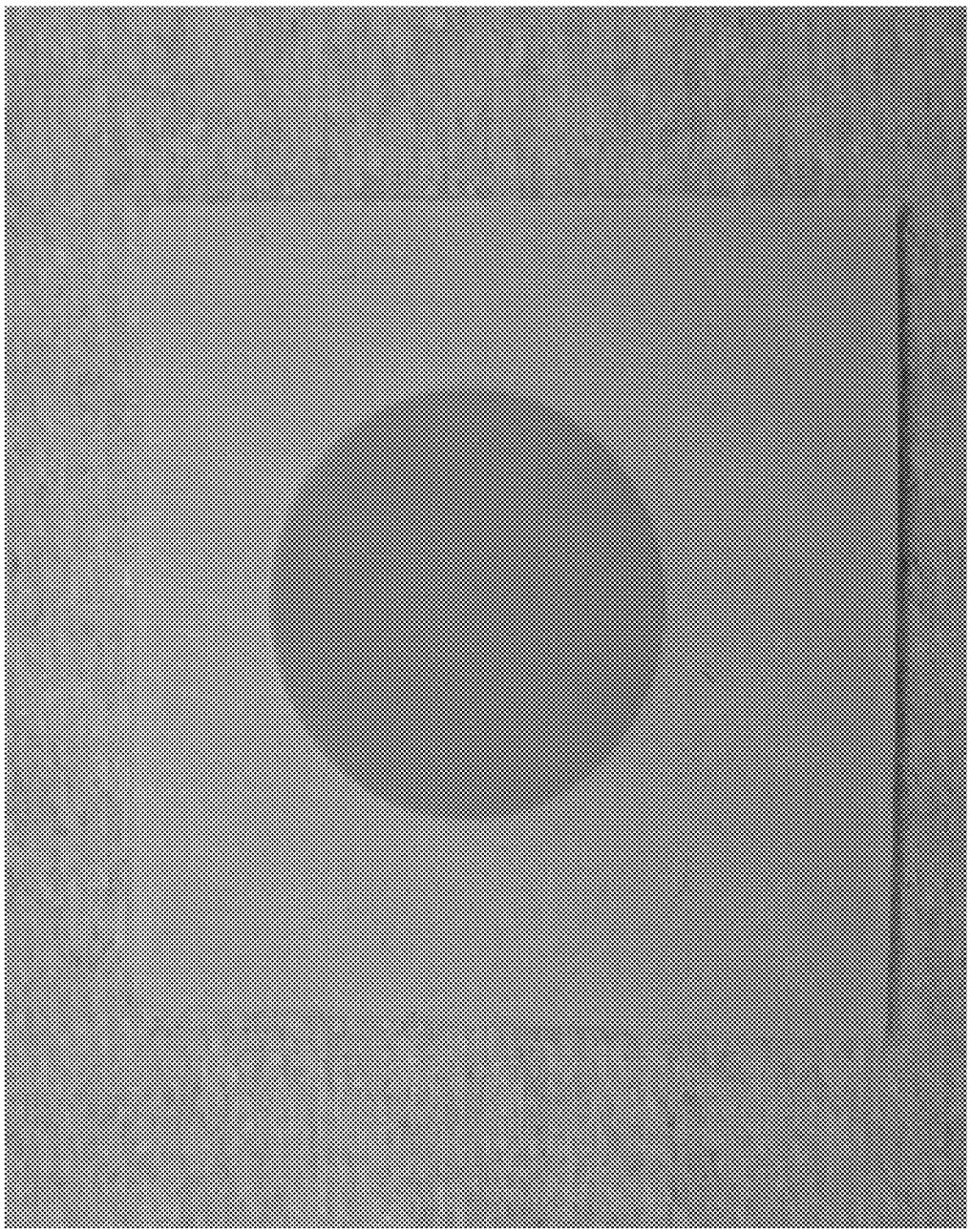
FIG. 14 is a photograph of a clean AAO membrane.

FIG. 12 is an example procedure for immobilizing gold nanoparticles on an AAO membrane. FIG. 13 shows the effect of immobilizing gold nanoparticles on a 13 mm AAO membrane without the use of surface stabilizing additives to prevent agglomeration. Agglomeration is particularly apparent on the outer surfaces of the membrane surface, i.e., the portions of the membrane between the pores. The gold nanoparticles agglomerate on the exterior surface of the membrane. The surface agglomeration makes the membrane ineffective. For reference, FIG. 14 is an example AAO membrane that has not been immobilized with gold nanoparticles. FIG. 14 may be compared with FIG. 9B to observe the differences between a clean AAO membrane and an AAO membrane with gold nanoparticles properly immobilized according to the procedure provided herein.

Figure 15:
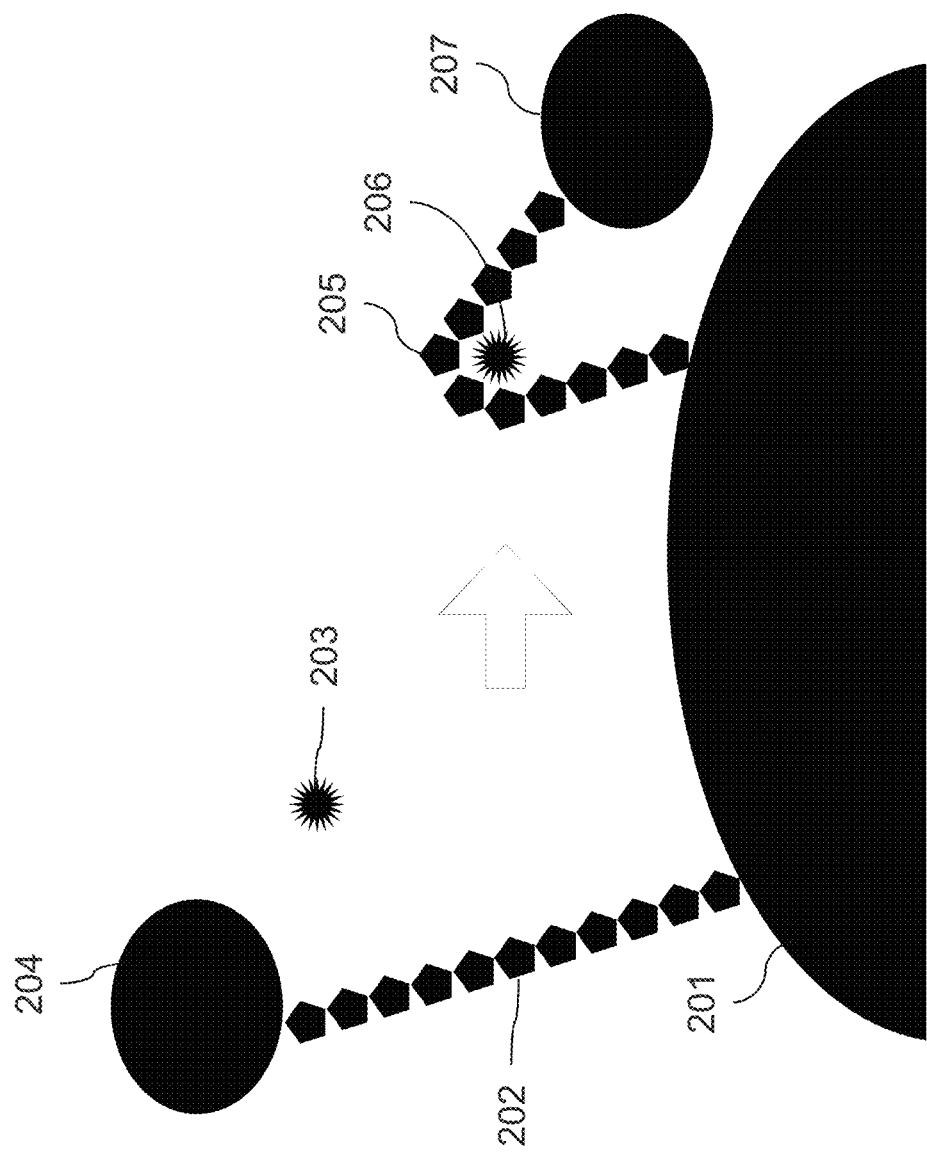
FIG. 15 is a diagram showing an example method to enhance the LSPR shift for small molecule targets.

Referring to FIG. 15, a method to enhance the LSPR shift for small molecule targets is outlined. For small molecular weight chemical target detection, for example ions or hormones, chemicals, DNA, RNA, aptamers or polymers 202 may not be effective without modification. However, a heavy molecule 204, such as a globular inert protein (bovine serum albumin), an inert heavy chained polymer or a surface inactivated small nanoparticle could be bound to the free end of the capture molecule 202 which may comprise, for example, an aptamer or capture polymer. When the target 203 comes into contact with the capture molecule 202, the capture molecule changes its conformation at 205, thereby bringing the heavy molecule 207 closer to the immobilized nanoparticle 201 surface. This enhances the LSPR effect that will be detectable by the spectrometer and allow for the detection of small chemical targets.

Another method of enhancing the LSPR signal for the detection of very small targets or targets at very low concentrations is the inclusion a signal-enhancing molecule that can be pumped into the mixture after target binding has taken place or mixed with the target prior to target binding. This is similar to the sandwich assay concept used in ELISA, where an immobilized antibody captures the target of interest and then a second molecular dye-labelled antibody is added to bind to the now immobilized target and signal its detection through fluorimetry. To adapt this concept to the sensor 106 as described herein, the sample fluid is pumped through the sensor and capture molecules on the nanoparticles bind the target chemicals. A secondary mixture of solution-based molecular dye labelled capture molecules are pumped through the sensor and bind to the captured targets. An energy transfer process occurs to enhance the LSPR effect due to the dye molecules being brought into close proximity with the metal nanoparticles. This may produce a larger absorption peak shift to be measured by the detector 110.

The incorporation of shift enhancers can also be used to improve the detection of chemicals. For example, a secondary capture molecules could be introduce to bind to the target after it has bound to the nanoparticle surface through the primary capture molecule. This would enhance the LSPR shift due to the enhanced localized change in the refractive index due to the additional mass. Another alternatives to potentially enhance the shift of the resonance peak is the addition of other enhancer entities, such as free-floating polymer or metal nanoparticles functionalized with secondary capture molecules, after the target chemicals are bound to the capture molecules in the sensor 106. Such entities would be made of materials with a high refractive index and molecular weight to allow a significant enhancement of the signal shift when they bind to the target. Metal particle enhancer entities could be made of an LSPR generating material to further enhance the resonance shift by resonance coupling. The entities could also be a magnetic material such as iron oxide, which has a very high refractive index and molecular weight. They could also be metal coated polymer particles, polymer coated metals particles, polymers particles, or metal particles.

Another method to enhance the performance of the LSPR sensor is to choose nanoparticle and pore sizes that cause the particles to be close enough together so that their three dimensional electromagnetic fields overlap. When this occurs, a single binding event on the surface of one nanoparticle will result in changes to its own electric field in addition to changes in the electromagnetic fields of those neighbouring nanoparticles close enough to have their fields overlap. This will result in a larger response from a single binding event, increasing the signal change.

Figure 20:
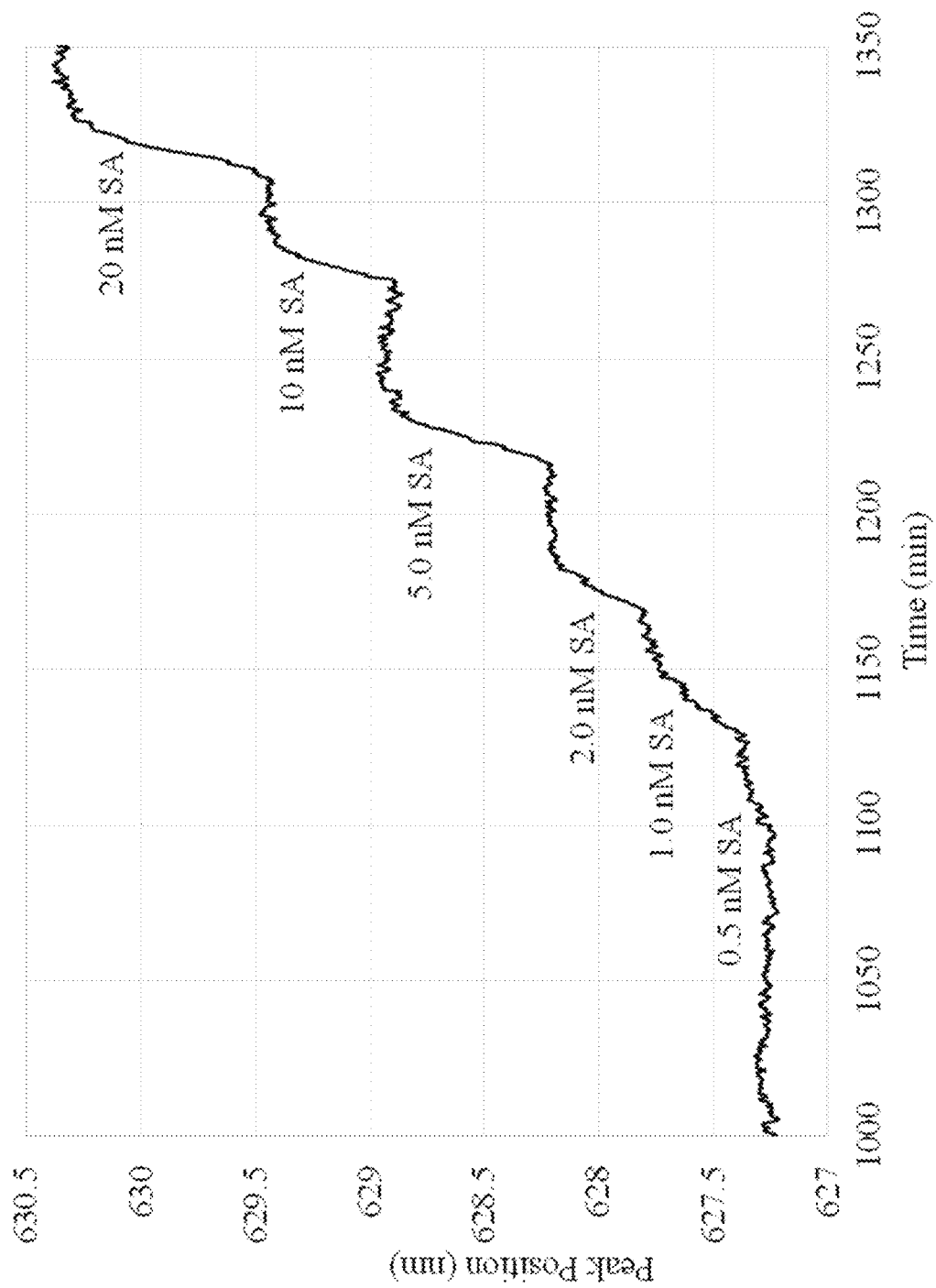
FIG. 20 shows the response of the T3D sensor to serial injections of the streptavidin (SA) protein, from 0.5 nM to 20 nM. The streptavidin binds to the biotinylated surface of the nanoparticles inside the AAO membrane.
Figure 21:
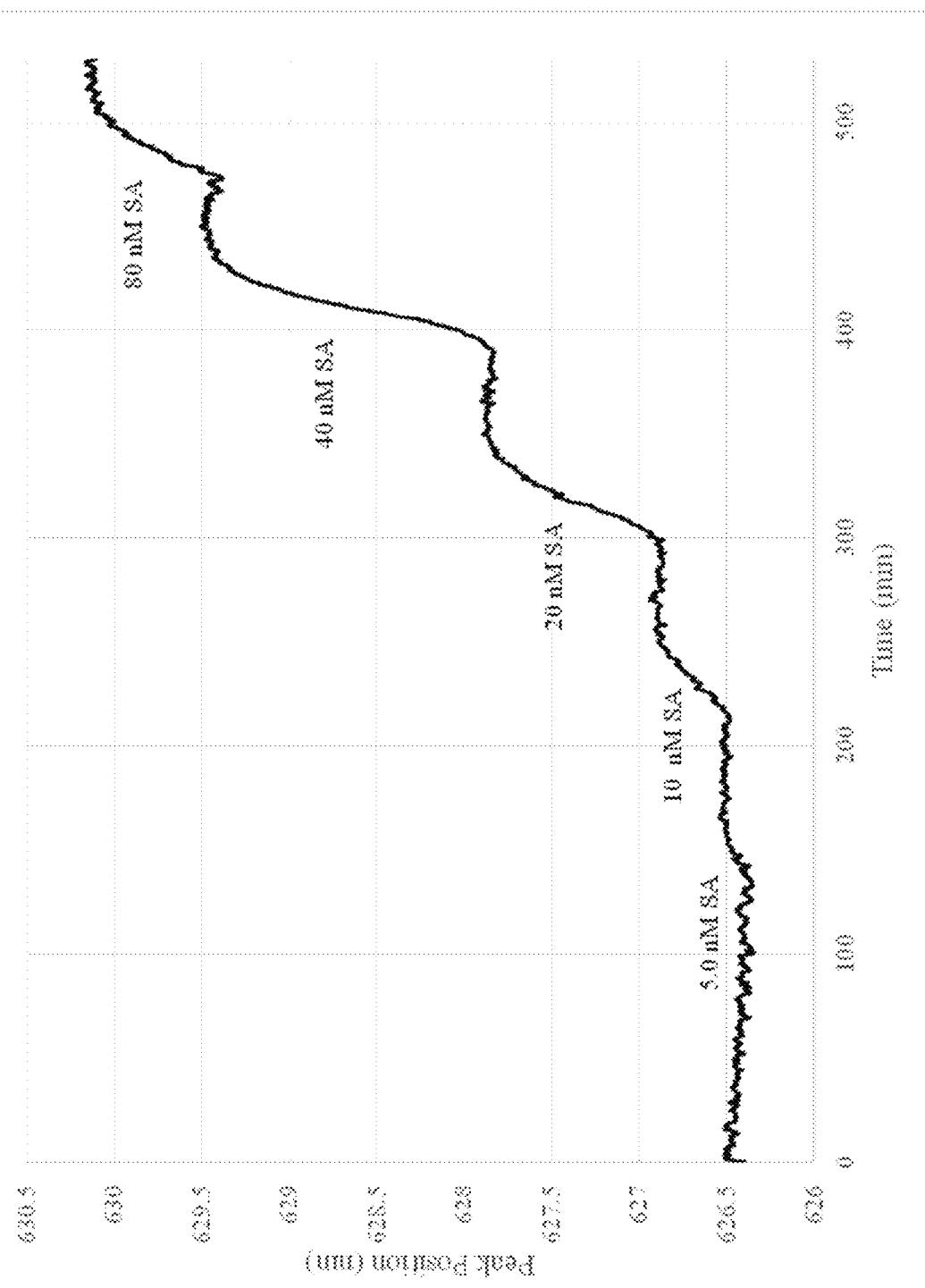
FIG. 21 shows the response of the conventional 2D sensor to serial injections of the streptavidin (SA) protein, from 5 nM to 80 nM. The streptavidin binds to the biotinylated surface of the nanoparticles which are immobilized onto a glass surface.

An example of the improvements offered by the T3D design versus the traditional 2D design is shown by comparison of FIG. 20 and FIG. 21. FIG. 20 shows serial additions of the protein streptavidin into an AAO membrane with 150 nm pores and 50 μm thick. Nanoparticles are immobilized in the pores and have an LSPR peak around 627 nm. The nanoparticles are functionalized with a biotin capture layer, with biotin being chemically bound to the nanoparticles via a thiol bond. The non-specific sites are blocked with PEG. The sensor shows a response at 0.5 nM streptavidin up to 20 nM in this case. 200 μL of streptavidin is introduced at 20 μL/min. The detection limit is approximately 0.5 nM for this system. FIG. 6X shows serial additions of streptavidin over a glass substrate with the same nanoparticles immobilized on the surface of the glass. Biotin is attached to the surface of the nanoparticles using the same chemistry as the T3D sensor. Streptavidin is injected serially at 20 μL/min in volumes of 200 μL. The sensor shows a response at 5.0 nM up to 80 nM in this case. The detection limit is approximately 5.0 nM. This demonstrates that the T3D sensor exhibits a 10× improvement in detection limit over the traditional 2D sensor, in this example case.

EXAMPLE 1

Test Protocol for Fibronectin LSPR Sensor Testing

Preparation Steps
Buffer Preparation ("Tris")
Buffer: 20 mM Tris, 100 mM NaCl, 0.005% Tween20, in nuclease free water, pH 7.4
1. Autoclave glassware and pipette tips (200 μL and 1000 μL) to ensure nuclease free conditions.
2. For a 500 mL mixture weigh: 1.21 g Tris, 2.92 g NaCl and 0.025 g Tween 20 dissolve into 500 mL of $dH_2O$ then measure the pH of the solution. Adjust the pH up or down to 7.4 using a NaOH or HCl solution.
3. Store in a sealed container at 4° C.
Fibronectin Protein Preparation
Stock: 0.5 mg/ml already dissolved in buffer
1. Aliquot into 54 μL volumes at 0.5 mg/ml in Tris Buffer (Aliquot concentration=1.14 μM)
2. Stored in −20° C. Freezer
BSA Preparation
1. Take 10.5 mg BSA, add to 2 ml vial, add 1 ml Tris buffer. This gives a 1% BSA solution. For a 0.1% solution add 70 uL of 1% BSA to 630 uL Tris buffer.
2. Store in a sealed container at 4° C.
Fibronectin Aptamer Preparation
Stock: 0.2 umol lypholized aptamer powder
1. Add 2 ml of Tris buffer to dry aptamer (makes 0.1 mM stock concentration).
2. Aliquot into 50 uL vials at 0.1 mM.
3. Stored at −20° C.
Functionalization and Testing Procedure
1. Thaw one aptamer aliquot to room temperature. Add 430 μL of Tris buffer to the aptamer aliquot to obtain a final concentration of 10 μM (once the 20 μL of TCEP is added in the next step). Vortex for 30 seconds to mix.
2. Make 2 ml of 40 mM stock TCEP by adding 20 mg TCEP to 2 ml of Tris buffer and mixing well. From this stock add 20 μL to the aptamer vial to give a final volume of 500 μL. Vortex for 30. Leave at room temperature for 2 hours.
3. Fill up a 20 ml beaker with water and place on the hot plate set at 90° C. Place the aptamer vial into the water bath for 3.5 minutes. Allow the aptamer to cool to room temperature.
4. Connect the T3D sensor and flow cell to the flow injection analysis system which consists of a 6 port injection valve, sample loop, and syringe pump. Set the pump speed to pump Tris buffer at 0.01 ml/min. Load 500 μL of aptamer solution into a 1 mL syringe ensuring no bubbles are present. Load the aptamer into a 500 μL sample loop and inject the solution via the injection valve. The interaction time between the gold nanoparticles and the aptamer will be approximately 50 minutes.
5. Once the solution has been fully pumped through the flow cell, pump fresh Tris buffer through the system for 30 minutes.

6. Turn the injection valve back to "load", and rinse out the sample loop using Tris buffer. Use a 1 ml syringe and load 500 μL of 0.1% BSA into the sample loop. Inject at a pumping speed of 0.01 ml/min.
7. Once the solution has been fully pumped through the flow cell (after 50 minutes hour), pump fresh buffer through the system for 30 minutes.
8. Disconnect the flow cell from the flow injection analysis system and remove the T3D sensor. Dry the sensor gently with nitrogen gas. If storing, store in a sealed container back filled with nitrogen.
9. Load the dry T3D sensor into the testing flow cell. Insert the flow cell into the reader unit and fill the cell with Tris buffer. Begin acquiring optical transmission spectra and begin tracking the LSPR peak position using the software. Acquire a baseline peak position in Tris buffer.
10. Add 550 μL of Tris buffer to a Fibronectin protein aliquot. This gives a Fibronectin concentration of 0.1 μM. Use a 1 ml syringe and load 200 μL of the Fibronectin sample into the inlet port of the flow cell. Activate the pump at 0.01 ml/min. The protein sample will pump through the membrane interact with the aptamer functionalized surface for 20 minutes.
11. Once the solution has been fully pumped through, acquire another peak baseline in Tris. Find the difference between the peak baseline from before and after the test. Using this value and the standard curve of concentration vs. peak shift, find the experimentally determine concentration of Fibronectin in the sample.
12. Dispose of the sensor and flow cell.

EXAMPLE 2

Test Protocol for Streptavidin LSPR Sensor Testing

Functionalization and Testing Procedure

Pump 10 mM 11-MUA (11-mercaptoundecanoic acid) and 1-OT (1-octanethiol) mixture (in a 3:1 ratio) in ethanol through the flow cell for 60 minutes at 0.01 ml/min.

Pump 13 mM PBS (phosphate buffered saline) through the flow cell for 30 minutes at 0.1 ml/min.

Pump a 5 mM EDC/NHS solution through the flow cell for 60 minutes at 0.01 ml/min.

Rinse with PBS for 30 minutes at 0.1 ml/min.

Pump 1 mM of Amine-PEG3-Biotin in 13 mM PBS at pH 6.5 at 0.01 ml/min for 50 minutes. (PEG—polyethylene glycol)

Rinse with 13 mM PBS at 0.1 ml/min for 30 minutes.

Pump 500 μL of 25 μM low molecular weight PEG at 0.01 ml/min.

Pump 13 mM PBS through the flow cell for 30 minutes at 0.1 ml/min.

Disconnect the flow cell from the flow injection analysis system and remove the T3D sensor. Dry the sensor gently with nitrogen gas. If storing, store in a sealed container back filled with nitrogen.

Load the dry T3D sensor into the testing flow cell. Insert the flow cell into the reader unit and fill the cell with PBS buffer. Begin acquiring optical transmission spectra and begin tracking the LSPR peak position using the software. Acquire a baseline peak position in buffer.

Load 200 μL of the streptavidin sample at 10 nM in PBS into the inlet port of the flow cell. Activate the pump at 0.01 ml/min. The protein sample will pump through the membrane interact with the functionalized surface for 20 minutes.

Once the solution has been fully pumped through, acquire another peak baseline in buffer. Find the difference between the peak baseline from before and after the test. Using this value and the standard curve of concentration vs. peak shift, find the experimentally determine concentration of streptavidin in the sample.

Dispose of the sensor and flow cell.

EXAMPLE 3

Immobilization of Gold Nanoparticles into AAO Membrane Pores Procedure

Take AAO membrane from storage, inspect for cracks, chips or weak points

Rinse AAO membrane with deionized $H_2O$ ($dH_2O$)

Load AAO membrane into flow cell and attach syringe connected to syringe pump

Pump 3 mL of $dH_2O$ through the membrane at 0.1 mL/min

Pump 2 mL of 2 μM poly-(succinyl-sulphonate)/0.4 μM $CaCl_2$ solution at pH 3.1 through the membrane at 0.1 mL/min Pump 6 mL of $dH_2O$ through the membrane at 0.1 mL/min Pump 2 mL of 2 μM polyallylamine hydrochloride/0.4 μM $CaCl_2$ solution at pH 3.1 through the membrane at 0.1 mL/min Pump 6 mL of $dH_2O$ through the membrane at 0.1 mL/min Remove membrane from flow cell, examine for cracks and rinse surface with $dH_2O$ Pipette 0.01% w/v bovine serum albumin solution onto the surface of the AAO membrane, leave for 1 minute then rinse with $dH_2O$ Load AAO membrane into flow cell in reverse orientation as previous and attach syringe connected to syringe pump Pump 3 mL of $dH_2O$ through the membrane at 0.1 mL/min Pump 10 mL of 0.1 nM gold nanoparticle mixture through the membrane at 0.05 mL/min Pump 6 mL of $dH_2O$ through the membrane at 0.1 mL/min If imaging: remove membrane from the flow cell, rinse with $dH_2O$ If testing: keep in flow cell and proceed to capture probe functionalization steps. Connect flow cell to flow injection analysis system.

Although examples are provided with reference to LSPR detection techniques, the above may also be adapted to other spectrometric detection assays, for example, ELISA.

Although the above has been described with reference to certain specific example embodiments, various modifications thereof will be apparent to those skilled in the art without departing from the scope of the claims appended hereto.

The invention claimed is:

1. A sensing apparatus comprising:
   i. at least one LSPR light source;
   ii. at least one detector; and
   iii. at least one sensor for LSPR detection of a target chemical located between the detector and the light source, the sensor comprising a substantially optically transparent, porous membrane, the membrane comprising nanoparticles immobilized on the surface of its pores, the nanoparticles being functionalized with one or more capture molecules
   wherein the detector detects light transmitted through the sensor.

2. The sensing apparatus of claim 1 wherein the membrane comprises anodized aluminum oxide.

3. The sensing apparatus of claim 1 wherein the pores are between 10 nm and 1000 nm in diameter.

4. The sensing apparatus of claim 1 wherein the nanoparticles are 1 to 1000 nm in diameter.

5. The sensing apparatus of claim 1 wherein the nanoparticles are selected from the group consisting of gold, silver, platinum, copper, gold-coated silver, silver-coated gold nanoparticles, and metal-coated non-metal nanoparticles.

6. The sensing apparatus of claim 1 wherein the nanoparticles are gold nanoparticles.

7. The sensing apparatus of claim 1 wherein the nanoparticle morphology is selected from the group consisting of spheres, rods, urchins, stars, rice, plates, decahedrons, hexagons, prisms, shells, platelets, triangles, cubes, cages and bipyramids.

8. The sensing apparatus of claim 1 wherein the nanoparticles are further functionalized with blocking molecules.

9. The sensing apparatus of claim 1 wherein the one or more capture molecules are selected from the group consisting of aptamers, antibodies, DNA, or polymers.

10. The sensing apparatus of claim 1 comprising two or more nanoparticle types having distinct LSPR peaks.

11. The sensing apparatus of claim 1 further comprising an LSPR shift enhancer.

12. The sensing apparatus of claim 1 further comprising an LSPR signal enhancer.

13. The sensing apparatus of claim 1 wherein the sensor is within a fluidic cartridge comprising a fluid inlet and a fluid outlet.

14. The sensing apparatus of claim 1 wherein the fluidic cartridge comprises multiple sensors.

* * * * *